US012611523B2

(12) United States Patent
Monteon et al.

(10) Patent No.: US 12,611,523 B2
(45) Date of Patent: Apr. 28, 2026

(54) ADVANCED 3-WAY STEERING

(71) Applicant: Cephea Valve Technologies, Inc.,
Abbott Park, IL (US)

(72) Inventors: Gabriel Monteon, Hollister, CA (US);
Randolf Von Oepen, Aptos, CA (US);
Francisco Valencia, East Palo Alto, CA
(US)

(73) Assignee: Cephea Valve Technologies, Inc.,
Abbott Park, IL (US)

( * ) Notice: Subject to any disclaimer, the term of this
patent is extended or adjusted under 35
U.S.C. 154(b) by 0 days.

(21) Appl. No.: 19/301,242

(22) Filed: Aug. 15, 2025

(65) Prior Publication Data

US 2025/0367408 A1      Dec. 4, 2025

Related U.S. Application Data

(63) Continuation of application No. 18/303,198, filed on
Apr. 19, 2023.

(60) Provisional application No. 63/340,552, filed on May
11, 2022.

(51) Int. Cl.
*A61M 25/01*      (2006.01)
*A61F 2/24*      (2006.01)
*A61M 25/00*      (2006.01)
(52) U.S. Cl.
CPC ....... *A61M 25/0147* (2013.01); *A61F 2/2427*
(2013.01); *A61M 25/0138* (2013.01); *A61M*
*2025/0042* (2013.01)
(58) Field of Classification Search
CPC .......... A61M 25/0147; A61M 25/0138; A61M
2025/0042; A61F 2/2427
See application file for complete search history.

(56) References Cited

U.S. PATENT DOCUMENTS

| | | | |
|---|---|---|---|
| 7,736,388 B2 | 6/2010 | Goldfarb | |
| 8,870,948 B1 | 10/2014 | Erzberger | |
| 2004/0044350 A1* | 3/2004 | Martin | ............... A61B 18/1492 |
| | | | 606/139 |
| 2006/0135961 A1* | 6/2006 | Rosenman | ......... A61B 17/0057 |
| | | | 604/95.04 |
| 2011/0137397 A1* | 6/2011 | Chau | ..................... A61F 2/2412 |
| | | | 623/2.37 |

(Continued)

FOREIGN PATENT DOCUMENTS

| | | |
|---|---|---|
| EP | 3927284 B1 | 7/2025 |
| WO | 2016183526 A1 | 11/2016 |

*Primary Examiner* — Suzette J Gherbi
(74) *Attorney, Agent, or Firm* — SLEMAN & LUND
LLP

(57) ABSTRACT

A medical device delivery system includes a steering catheter including a first steering ring having a plurality of apertures positioned in the wall of the first steering ring. The plurality of apertures are positioned at spaced distances around a circumference of the first steering ring. A first steering cable passes through a first one of the apertures, and a first return cable passes through a second one of the apertures. A second steering cable passes through a third one of the apertures, and a second return cable passes through a fourth one of the apertures. The first steering cable is positioned about 180 degrees from the second steering cable. A handle is operably coupled to a proximal end of the steering catheter. A first control member controls the first steering and first return cable, and a second control member controls the second steering and second return cable.

20 Claims, 19 Drawing Sheets

(56)  References Cited

U.S. PATENT DOCUMENTS

| | | | | |
|---|---|---|---|---|
| 2014/0088684 A1* | 3/2014 | Paskar | ...................... | A61F 2/95 |
| | | | | 604/95.05 |
| 2015/0164639 A1* | 6/2015 | Starksen | .............. | A61B 17/068 |
| | | | | 623/2.11 |
| 2016/0158000 A1 | 6/2016 | Granada | | |
| 2018/0028177 A1* | 2/2018 | van Oepen | ......... | A61M 25/005 |
| 2018/0071098 A1* | 3/2018 | Alon | ..................... | A61F 2/2433 |
| 2018/0092744 A1 | 4/2018 | Von Oepen | | |
| 2018/0126095 A1 | 5/2018 | Von Oepen | | |
| 2020/0155803 A1 | 5/2020 | Caton | | |
| 2020/0155804 A1* | 5/2020 | von Oepen | ........... | A61F 2/2439 |
| 2020/0323634 A1 | 10/2020 | Von Oepen | | |
| 2021/0322166 A1* | 10/2021 | von Oepen | ........... | A61F 2/9524 |
| 2021/0361404 A1 | 11/2021 | Haynes | | |
| 2023/0030110 A1 | 2/2023 | Hake | | |
| 2023/0364387 A1* | 11/2023 | Monteon | ........... | A61M 25/0147 |
| 2025/0205051 A1* | 6/2025 | Cobar | ................... | A61F 2/2436 |

* cited by examiner

26

57   120   121          119   118   124

28

134
129
126
132   130   128

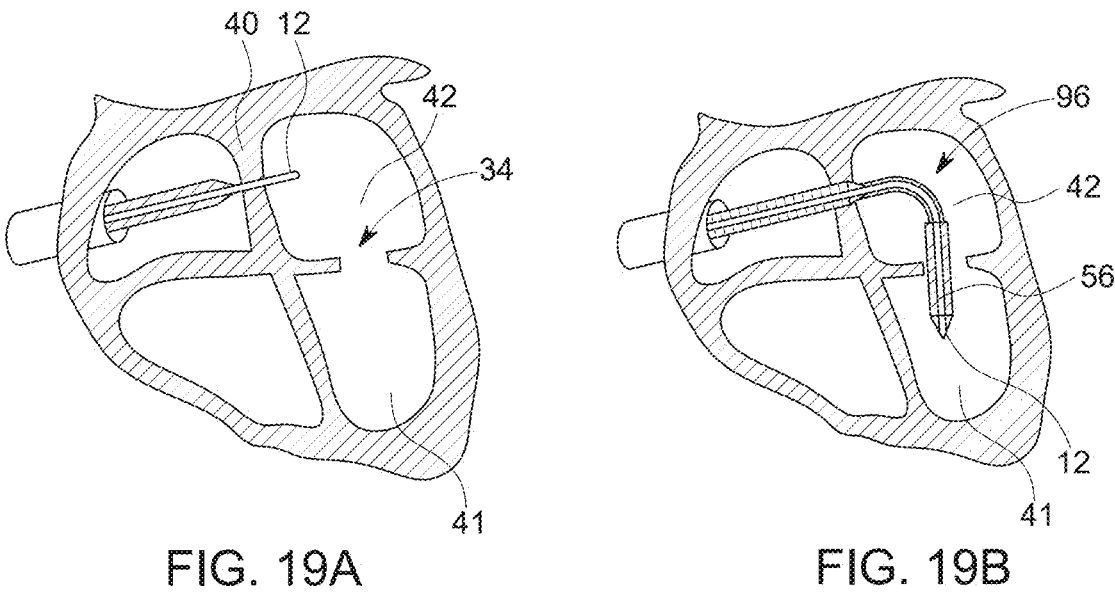
FIG. 19A                    FIG. 19B
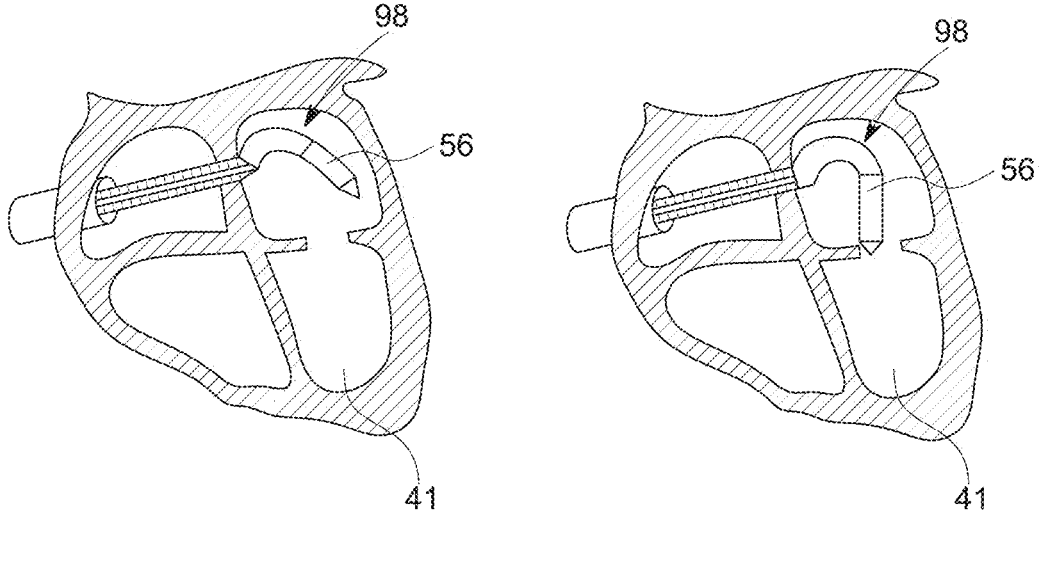
FIG. 19C                    FIG. 19D

ADVANCED 3-WAY STEERING

CROSS-REFERENCE TO RELATED APPLICATIONS

This application is a continuation of U.S. patent application Ser. No. 18/303,198, filed Apr. 19, 2023, which claims priority to the filing date of U.S. Provisional Patent Application No. 63/340,552, filed May 11, 2022, the disclosures of which are both hereby incorporated by reference herein.

BACKGROUND OF THE DISCLOSURE

The present disclosure generally relates to devices, systems, and methods for delivering an intravascular medical device into a patient for implantation. More particularly, the present disclosure relates to devices, systems, and methods for steering a transcatheter delivery device of a collapsible prosthetic heart valve to a native heart valve annulus.

Intravascular medical devices that are collapsible can be delivered into a patient less invasively than devices that are not collapsible. For example, a collapsible prosthetic heart valve may be delivered into a patient via a tube-like delivery apparatus such as a catheter, a trocar, a laparoscopic instrument, or the like. Intravascular delivery can avoid the need for a more invasive procedure, such as an open-chest, open-heart surgery, and thereby reduce the risks, costs, and time associated with open-heart surgical procedures.

Intravascular delivery devices, such as a steerable catheter, may benefit from precise steering mechanisms to properly position the medical device within the patient. If precise steering maneuvers are not implemented, the delivery location may be unreachable or further damage may result to the patient. These steering mechanisms may include cables that are fed through holes in a series of rings. An operator can adjust a distal end of the catheter by operating a series of controls attached to a handle or body of the steerable catheter. These controls tense and relax the cables to cause deflection in at least one direction of the distal end of the catheter.

A safe, accurate, and efficient delivery system and method for placing an intravascular medical device that addresses some or all of the foregoing concerns is described herein.

BRIEF SUMMARY OF THE INVENTION

According to one aspect of the present invention, a medical device delivery system comprises a steering catheter including: a first steering ring having a proximal end, a distal end, an outer surface, an inner surface, a wall defined between the outer surface and inner surface, and a central lumen defined by the inner surface along a longitudinal direction; a plurality of apertures positioned in the wall of the first steering ring, the plurality of apertures positioned at spaced distances around a circumference of the first steering ring; a first steering cable passing through a first aperture of the plurality of apertures, and a first return cable passing through a second aperture of the plurality of apertures; a second steering cable passing through a third aperture of the plurality of apertures, and a second return cable passing through a fourth aperture of the plurality of apertures, wherein the first steering cable is positioned about 180 degrees from the second steering cable; and a handle operably coupled to a proximal end of the steering catheter, the handle including: a first control member, the first steering cable and the first return cable coupled to the first control member so that actuation of the first control member in a first direction pulls the first steering cable, and actuation of the first control member in a second direction opposite the first direction pulls the first return cable; a second control member, the second steering cable and the second return cable coupled to the second control member so that actuation of the second control member in a third direction pulls the second steering cable, and actuation of the second control member in a fourth direction opposite the third direction pulls the second return cable.

In another aspect, the system further comprises a third steering cable passing through a fifth aperture of the plurality of apertures of the first steering ring and a third return cable passing through a sixth aperture of the plurality of apertures.

In a different aspect, the system further comprises a third control member, the third steering cable and the third return cable coupled to the third control member so that actuation of the third control member in a fifth direction pulls the third steering cable, and actuation of the second control member in a sixth direction opposite the fifth direction pulls the third return cable.

In another aspect, the system further comprises a second steering ring, the second steering ring spaced apart from the first steering ring in a longitudinal direction and including a proximal end, a distal end, an outer surface, an inner surface, a wall defined between the outer surface and inner surface, a central lumen defined by the inner surface along a longitudinal direction, and a plurality of apertures positioned in the wall at spaced distances around a circumference of the second steering ring.

In a different aspect, the second steering cable extends through a first aperture of the second steering ring and the second return cable extends through a second aperture of the second steering ring.

In another aspect, the first steering cable extends through a third aperture of the second steering ring and the first return cable extends through a fourth aperture of the second steering ring.

In a further aspect, the first aperture of the second steering ring and the third aperture of the second steering ring are diametrically opposed to each other and the second aperture of the second steering ring and the fourth aperture of the second steering ring are diametrically opposed to each other.

In another aspect, the system further comprises a third steering ring, the third steering ring spaced apart from the first steering ring and the second steering ring in a longitudinal direction and including a proximal end, a distal end, an outer surface, an inner surface, a wall defined between the outer surface and inner surface, a central lumen defined by the inner surface along a longitudinal direction, and a plurality of apertures positioned in the wall at spaced distances around a circumference of the third steering ring.

In a different aspect, the first steering cable extends through a first aperture of the third steering ring and the first return cable extends through a second aperture of the third steering ring.

In another aspect, actuation of the first control member in the first direction pulls the first steering ring, actuation of the second control member in the third direction pulls the second steering ring, and actuation of the third control member in the fifth direction pulls the third steering ring.

In a further aspect, each of the first steering ring, the second steering ring, and the third steering ring comprises a step between each aperture of the pairs of apertures.

In another aspect, the system further comprises a hypotube having a proximal section, an intermediary section, and distal section.

In a different aspect, the proximal section has slits to allow for bending of the hypotube corresponding to a pull direction of the first steering ring, the intermediary section has slits to allow for bending of the hypotube corresponding to a pull direction of the second steering ring, and the distal section has slits to allow for bending of the hypotube corresponding to a pull direction of the third steering ring.

In a further aspect, each of the first control member, the second control member, and the third control member is a knob.

In another aspect, the first and second apertures of the third steering ring are offset from each other an angle equal to an angle between the third and fourth apertures in the second steering ring.

In a different aspect, bending of the hypotube corresponding to the pull direction of the second steering ring is coplanar with the bending direction of the hypotube corresponding to the pull direction of the third steering ring.

According to another aspect of the invention, a method of positioning a medical device at a delivery location using a steering catheter comprises actuating a first control member operably coupled to a first steering cable and first return cable, the first steering cable and first return cable extending distally from the first control member to a plurality of apertures in a first ring, wherein actuating the first control member in a first direction pulls the first steering cable and actuating the first control member in a second direction pulls the first return cable; actuating a second control member operably coupled to a second steering cable and second return cable, the second steering cable and second return cable extending distally from the second control member through the plurality of apertures in the first ring to a plurality of apertures in a second ring, wherein actuating the second control member in a first direction pulls the second steering cable and actuating the second control member in a second direction pulls the second return cable; and actuating a third control member operably coupled to a third steering cable and third return cable, the third steering cable and third return cable extending distally from the third control member through the plurality of apertures in the first ring and the plurality of apertures in the second ring to a plurality of apertures in a third ring, wherein actuating the third control member in a first direction pulls the third steering cable and actuating the third control member in a second direction pulls the third return cable.

In another aspect, the method further comprises extending an extension catheter distally from the steering catheter to deliver a medical device.

According to another aspect of the invention, a method of implanting a prosthetic atrioventricular valve into a patient comprises positioning a valve cover of a delivery device in or adjacent a native atrioventricular valve annulus of the patient while the prosthetic atrioventricular valve is in a collapsed condition within the valve cover; withdrawing the valve cover to expose a ventricular anchor of the prosthetic atrioventricular valve, the ventricular anchor being restricted from self-expansion upon being exposed; further withdrawing the valve cover to expose an atrial anchor of the prosthetic atrioventricular valve, the atrial anchor self-expanding and deploying upon being exposed; advancing the prosthetic atrioventricular valve distally until the self-expanded and deployed atrial anchor contacts tissue on an atrial side of the native atrioventricular valve annulus; and after the atrial anchor contacts tissue on the atrial side of the native atrioventricular valve annulus, releasing the restriction on the ventricular anchor to allow the ventricular anchor to self-expand and deploy into contact with a ventricular side of the native atrioventricular valve annulus.

BRIEF DESCRIPTION OF THE DRAWINGS

FIGS. 19A-D are cross-sectional views of the human heart of FIG. 3 and the distal end of the catheter of FIG. 1 in various stages of delivery.

DETAILED DESCRIPTION

As used herein, the term "inflow end," when used in connection with a prosthetic heart valve, refers to the end of the heart valve through which blood enters when the heart valve is functioning as intended, whereas the term "outflow end," when used in connection with a prosthetic heart valve, refers to the end of the heart valve through which blood exits when the heart valve is functioning as intended. For a prosthetic mitral valve, the inflow end is closest to the left atrium when the heart valve is implanted in a patient, and the outflow end is closest to the left ventricle when the heart valve is implanted in a patient. Further, when used herein in connection with a delivery device, the terms "proximal" and "distal" are to be taken as relative to a user operating the device in an intended manner. "Proximal" is to be understood as relatively close to the user and "distal" is to be understood as relatively farther away from the user. Also as used herein, the terms "substantially," "generally," and "about" are intended to mean that slight deviations from absolute are included within the scope of the term so modified.

In the description which follows, a delivery system and the components thereof are described in connection with the delivery, positioning, and deployment of a prosthetic mitral valve at the native mitral valve annulus. However, it is to be understood that the delivery system and components described also may be used to deliver, position, and deploy other cardiac valves, such as the aortic valve, the pulmonary valve, and the tricuspid valve, as well as other medical devices. Exemplary prosthetic heart valves that can be used with the delivery system described herein include the expandable prosthetic heart valves described in U.S. Pat. Pub. No. 2016/0158000; in U.S. Pat. No. 8,870,948; and in PCT Pub. No. WO 2016/183526, the disclosures of all of which are hereby incorporated by reference herein.

Figure 1:
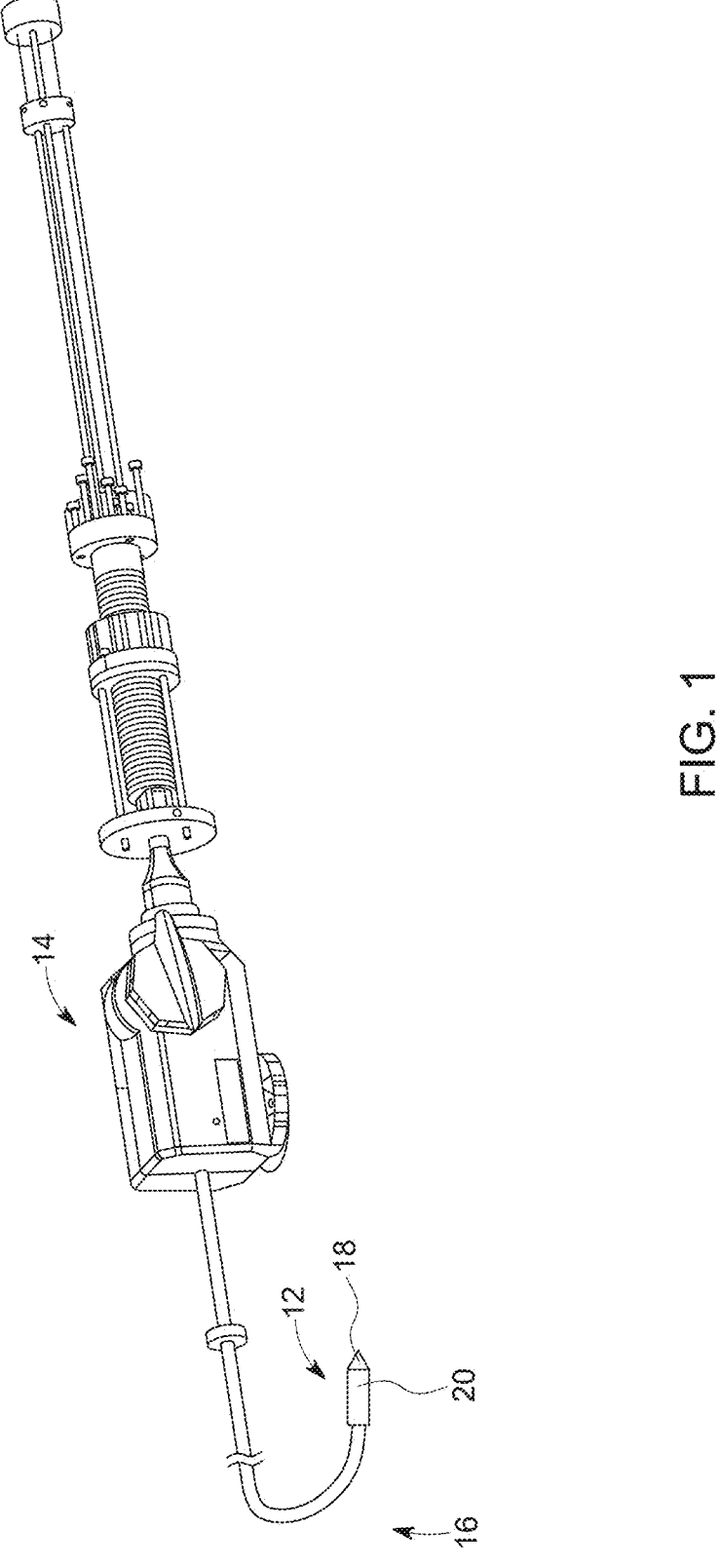
FIG. 1 is a perspective view of a catheter delivery device, according to one embodiment.

FIG. 1 illustrates a perspective view of a delivery system 10 for delivering, positioning, and deploying an exemplary prosthetic heart valve 20 in a patient, and then extracting a distal end 12 of the delivery system 10 out of the patient. It should be understood that, in FIG. 1, the prosthetic heart valve 20 is positioned within a valve cover of the delivery system 10, and thus the lead line for part number 20 points to the position of the collapsed prosthetic heart valve, which is not visible in FIG. 1 due to it being covered. Delivery system 10 generally includes a handle assembly 14 and a catheter assembly 16. Catheter assembly 16 extends from a proximal end of handle assembly 14. The distal end of catheter assembly 16 includes an atraumatic tip 18 and a plurality of catheter and/or hypotube components that are longitudinally slidable relative to each other and that provide different functionality during operation of delivery system 10 to enable effective delivery and deployment of a prosthetic heart valve 20, such as a prosthetic mitral valve.

Figure 2:
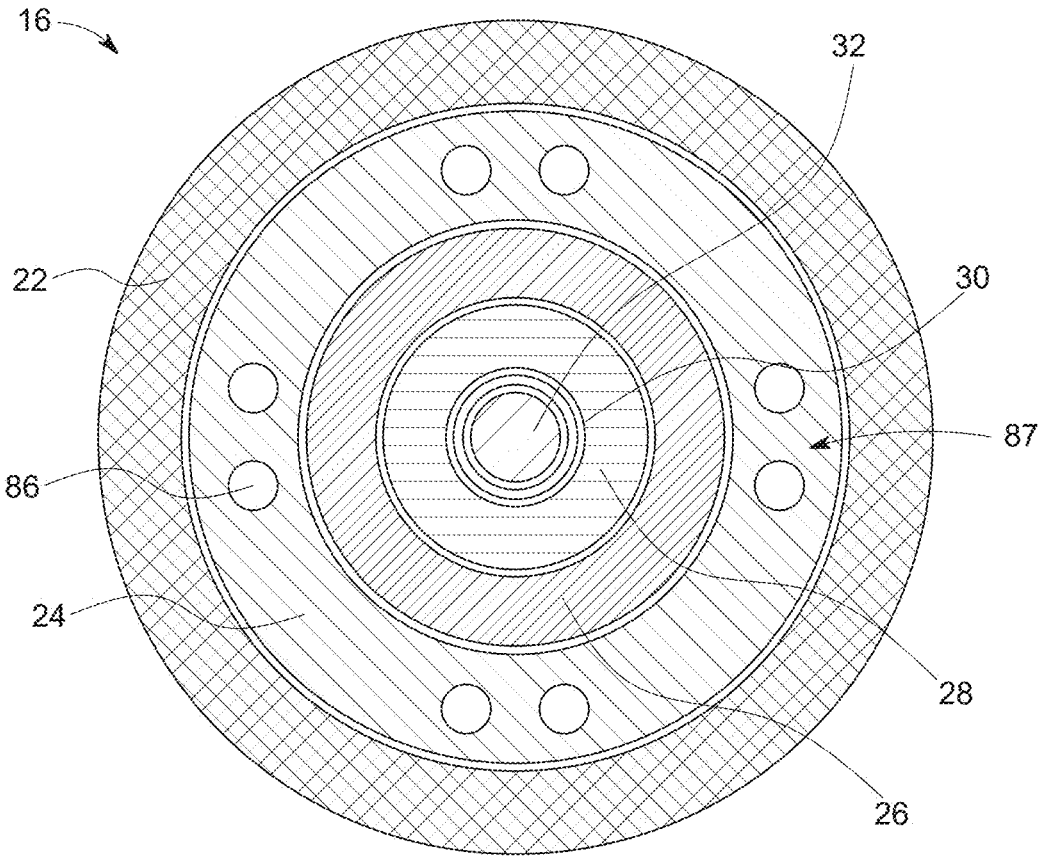
FIG. 2 is a cross-section view of the catheter of FIG. 1.

FIG. 2 shows a cross-sectional view of catheter assembly 16. Catheter assembly 16 includes the components of an outer sheath 22, a steering catheter 24, an extension catheter 26, a suture catheter 28, and a nosecone catheter 30, each catheter concentric and nested sequentially within another. As illustrated, nosecone catheter 30 has a lumen sized to receive a guidewire 32 therein. Each of these components is described in further detail below. It should be understood that the illustration of FIG. 2 is of a system with two-way steering, as opposed to the three-way steering described in more detail below.

Figure 3:
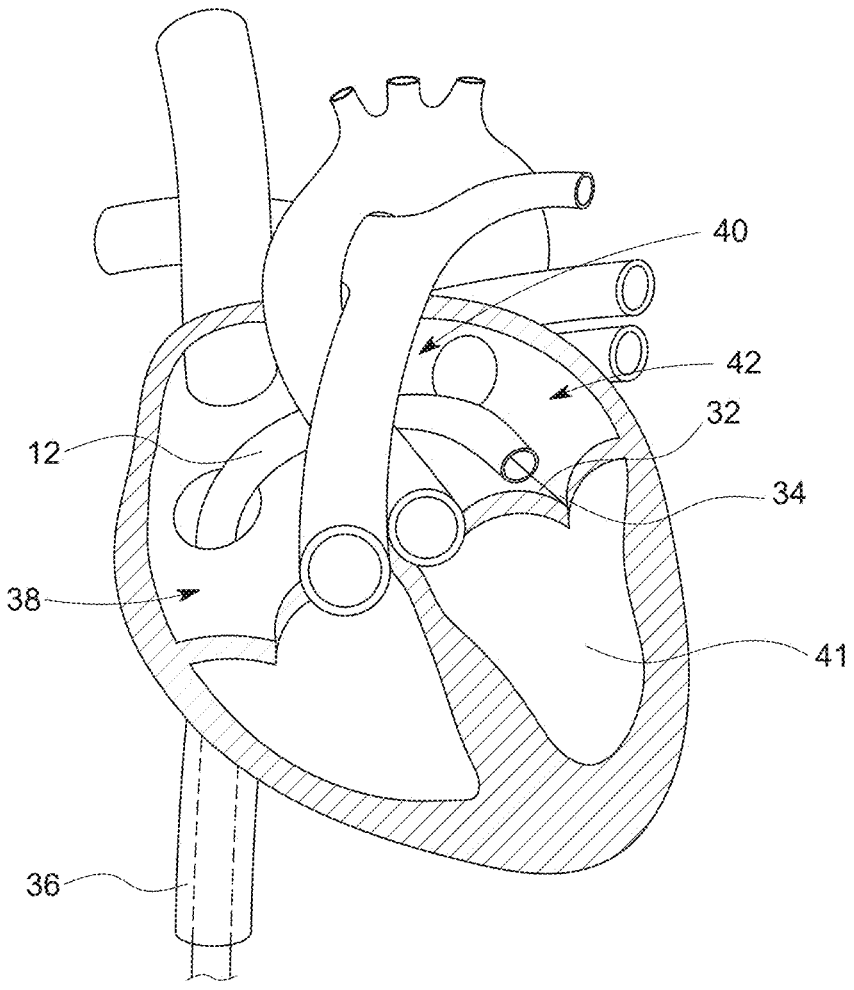
FIG. 3 is a cross-section view of a human heart.
Figure 4:
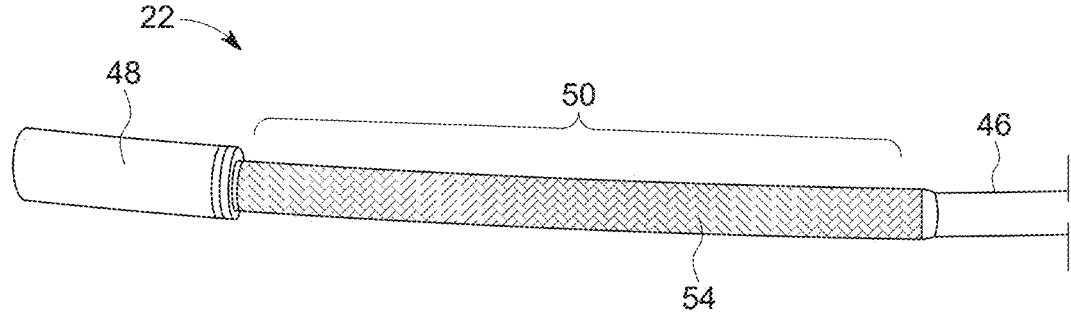
FIG. 4 is a perspective view of the outer sheath of the catheter of FIG. 1.

FIG. 3 shows a schematic representation of a patient's heart and a delivery route that may be followed by catheter assembly 16 to reach the native mitral valve annulus 34. Using a transfemoral approach, catheter assembly 16 may be inserted into the patient's femoral vein and advanced through the inferior vena cava 36 to the right atrium 38. Catheter assembly 16 is then advanced through a puncture made in atrial septum 40, into left atrium 42 and to the native mitral valve annulus 34.

In other implementations, such as for a procedure associated with a tricuspid (i.e. right atrioventricular) valve, catheter assembly 16 may be advanced through the inferior vena cava 36 and into the right atrium 38, where it may then be positioned and used to perform the procedure related to the tricuspid valve. Although many of the examples described herein relate to medical device delivery at the native mitral valve annulus 34, one or more embodiments may be utilized in other cardiac procedures, including those involving the tricuspid valve or other cardiac valves.

Although one preferred method for accessing a targeted cardiac valve annulus is a transfemoral approach, it will be understood that the embodiments described herein may also be utilized where alternative approaches are used. For example, embodiments described herein may be utilized in a transjugular approach, transapical approach, transradial approach, or other suitable approaches to the targeted anatomy. For procedures relating to the mitral valve or tricuspid valve, the delivery of the prosthetic heart valve or other medical device is preferably carried out from an atrial aspect (i.e., with the distal ends of catheter assembly 16 positioned within the atrium superior to the targeted valve). The illustrated embodiments are shown from such an atrial aspect. However, it will be understood that the delivery of the medical devices described herein may also be carried out from a ventricular aspect. In some circumstances, it is preferable to use a delivery route that avoids the requirement of making an incision in the chest and puncturing the left or right ventricle to access the desired valve being replaced. In other words, intravascular routes, such as via the femoral vein, may be less traumatic as they do not require chest incisions or puncturing the left or right ventricle of the heart.

Additional details regarding delivery systems and devices that may be utilized in conjunction with the components and features described herein are described in U.S. Patent Publication Nos. 2018/0028177, 2018/0092744, and 2020/0155804, the disclosures of which are hereby incorporated by reference herein.

As depicted in FIG. 2, the outermost component of the catheter assembly 16 is outer sheath 22. Outer sheath 22 extends from a proximal end 46 to a distal end 48. A proximal portion of the outer sheath 22 is formed by a hypotube having a plurality of laser cut slits 44 along its length. Slits 44 may be preferably cut in an interrupted spiral pattern so as to define a longitudinally continuous spine along the length of proximal portion. Slits 44 may begin at a spaced distance from proximal end 46 of outer sheath 22 so that the proximal end of the outer sheath can be connected to a hemostasis valve (not shown) with a leakproof seal. In some embodiments, the hypotube has two spines spaced 180° apart, with on one side of the spine (the direction in which the hypotube will not bend) having slits and on the other side (direction of the bend) it will have cut-outs to allow for the hypotube to bend. However, the words "slits" as used herein generally applies to cutouts that allow for a bending operation, or a return-to-straight operation after bending. At least one fixation ring may be located around the outside of proximal portion. The fixation ring may act to locate delivery system 10 within a stabilizer structure 11 that holds the delivery system 10 stationary during an insertion and deployment procedure, as will be discussed further below.

A distal portion of outer sheath 22 is a bending portion 50 extending from the proximal portion to the distal end 48 of the outer sheath 22. Distal portion has a sufficient length to surround and extend along the portion of catheter assembly 16 that is designed to bend and deform to navigate through a patient's vasculature and heart to reach the mitral valve annulus for deployment of the prosthetic heart valve. Bending portion 50 may have an inside layer formed from a coiled wire and an outer braided layer covering the coiled layer. Coiled layer may have spaces between adjacent turns of the coil. This structure preferably exhibits a high degree of flexibility. Further, coiled layer keeps bending portion 50 round when it is bent, preventing it from assuming an oval shape or another shape that could make it difficult to retract outer sheath 22 to deploy the prosthetic heart valve 20. As outer sheath 22 is retracted to deploy the prosthetic heart valve 20, internal friction will inhibit the retraction of coiled layer, causing braided layer to lengthen. As the braided layer lengthens, its diameter will collapse around coiled layer, allowing high tension forces without ovalizing even in a bend configuration. On the other hand, in the event a resheathing procedure becomes necessary, as the prosthetic heart valve is drawn into valve cover 56 (described below), the spaces between the turns of the coils in coiled wire will compress.

A stainless-steel ring may be laser welded to the proximal end of coiled layer. A bushing (not shown) is uncovered by braided sleeve to enable the proximal end of bending portion 50 to be laser welded to the proximal portion 46 of outer sheath 22. Another stainless-steel ring may be laser welded to the distal end of coiled layer, followed by another stainless-steel ring that has a slightly smaller diameter and is externally threaded. The external threads provide for threaded connection of a valve cover 56 to bending portion 50, and the slightly smaller diameter of ring enables the connection to be made without any exposed edges.

Figure 20:
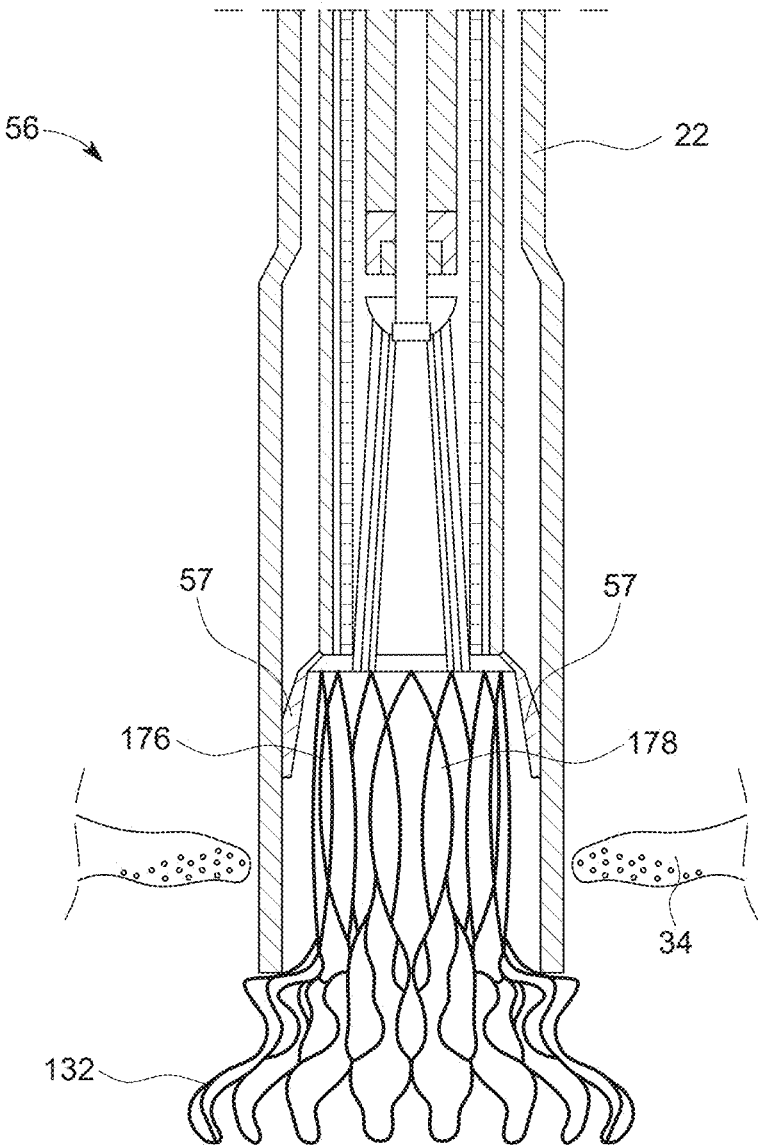
FIG. 20 is a cross sectional view of a valve cover of FIG. 1.

Valve cover 56, shown in FIG. 20, defines a compartment for housing prosthetic heart valve 20 in a compressed state prior to intravascular delivery of the prosthetic valve to the targeted cardiac site. Valve cover 56 may be formed by milling a solid rod of a hard, lightweight metal, such as grade 5 titanium, to form a generally cylindrical very thin-walled tube having an inner diameter and length sized to receive the prosthetic mitral valve in a collapsed condition. The titanium rod may be milled to a wall thickness of between about 0.20 mm and about 0.50 mm, or between about 0.30 mm and about 0.40 mm. A valve cover 56 having a wall thickness within the foregoing ranges may be sufficiently echotransparent to enable echocardiographic visualization of prosthetic heart valve 20 when loaded therein during a procedure. A series of internal threads may be cut at the proximal end of valve cover 56 for engagement with the external threads at the distal end of outer sheath 22.

Titanium is sufficiently hard that it will not interact with or contaminate, or is less likely to interact with or contaminate, the nitinol forming the frame of prosthetic heart valve 20 as the valve is retracted into and held within valve cover 56. A series of V-shaped cuts may be laser cut along one side of valve cover 56, and a series of slits may be laser cut along the diametrically opposed side of the valve cover, leaving a pair of continuous longitudinal spines along opposite sides of the valve cover. Cuts and slits may be formed by a short-pulse laser that sublimes the metal, thereby avoiding any remelt in the interior of valve cover 56. Additionally, on the last pass of laser cutting the laser beam may be defocused to smooth the edges of cuts and slits. The series of cuts and slits enable valve cover 56 to bend in a single plane. As valve cover 56 bends, cuts will collapse, while slits will open. Preferably, cuts and slits are sufficient to enable valve cover 56 to bend between at least 75° to 120° or more (including up to 150° for the three-way steering configuration described below), in order to properly orient prosthetic heart valve 20 superior to mitral valve annulus 34 for deployment. Cuts and slits are not formed along a distal section of valve cover 56 so as to not interfere with the protruding tines of the prosthetic heart valve 20 as the prosthetic valve is retracted into the valve cover. After the formation of cuts and slits, valve cover 56 may be deburred, preferably using a mechanical honing process, to soften any sharp edges and remove any extraneous metal.

The spines formed along opposite sides of valve cover 56 between cuts and slits provide the valve cover with sufficient tensile strength to withstand the retraction of outer sheath 22 during deployment of a prosthetic heart valve. The distal end of valve cover 56 has a number of external threads to attach a loading funnel (described below) to the valve cover. After a prosthetic mitral valve has been loaded into valve cover 56 and the funnel has been removed, a tantalum ring may be threaded onto the distal end of the valve cover. The ring helps the user locate the end of valve cover 56 under x-rays or ultrasound imaging to assure the proper location and orientation of the valve cover for deployment of the prosthetic valve.

The entire length of outer sheath 22 and valve cover 56 may be covered by a flexible, fluid-impermeable layer to seal slits 44 in the proximal portion and coil/braid portion in the bending portion 50 of the outer sheath and the cuts and slits in the valve cover. Alternatively, the layer may extend only from valve cover 56 to a location just proximal of coil/braid portion. In yet another arrangement, the layer may be interposed between the coiled layer and braided sleeve of outer sheath 22. Any of these arrangements may be employed, as long as a liquid-tight structure results. The layer may be formed from a tube of Texin® synthetic resin available from Mobay Chemical Company, or from another elastic and/or polymeric material. After the application of the layer, the proximal and distal ends of the tube may be bonded to the underlying structure using thermal adhesives, UV-bonded adhesives, other types of adhesives, thermal boding, heat shrinking or other techniques. Subsequently, the layer may be cleaned by a plasma treatment process and a hydrophilic coating may be applied thereover.

Figure 5:
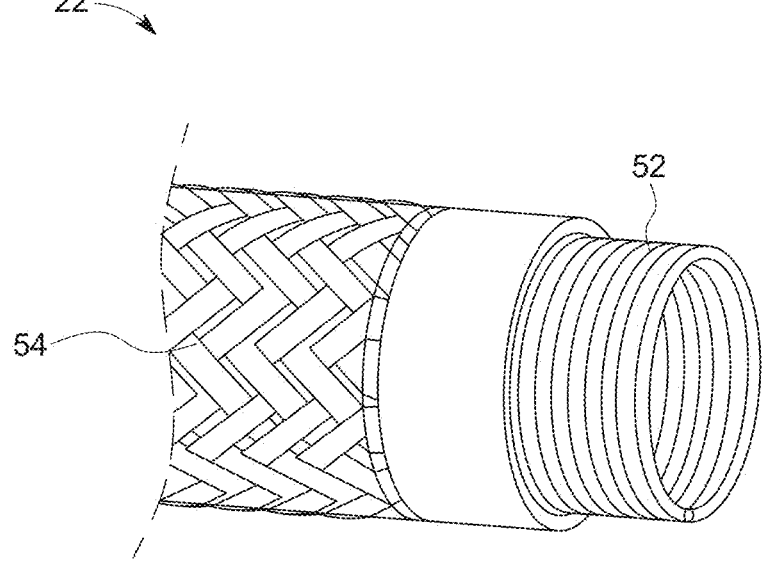
FIG. 5 is an enhanced view of the outer sheath of FIG. 4 showing the outer sheath's inner components.
Figure 6:
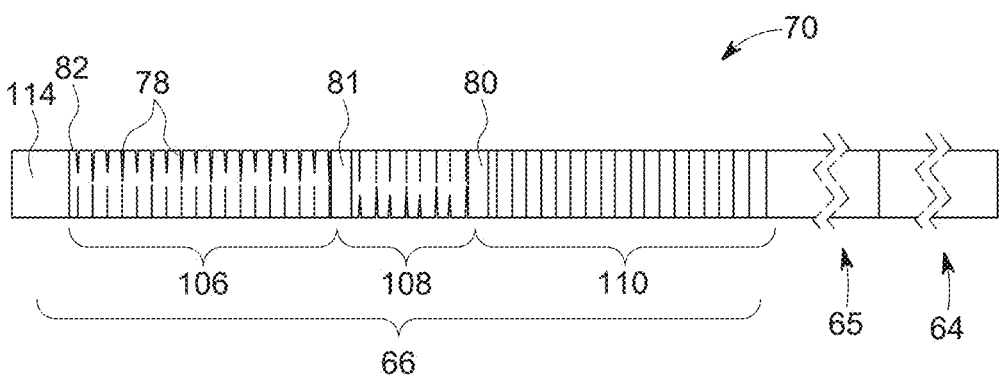
FIG. 6 is a side perspective view of the steering catheter of FIG. 1.

As depicted in FIGS. 5 and 6, a steering catheter 24 may be concentrically nested within outer sheath 22 and is configured to be selectively curved to facilitate navigation through the patient's vasculature and portions of the heart. Steering catheter 24 may be formed from a stainless steel hypotube 70 extending from a proximal section 64 that is connected to steering catheter handle 68 to a distal section 66. The proximal section 64 is uncut and is sealed within a steering catheter handle 68. The uncut portion of proximal section 64 provides steering catheter 24 with a desired amount of stiffness, torqueability and pushability, as well as the ability to form a leakproof connection with steering catheter handle 68. The uncut portion may be primarily for sealing. In other words, although it is true that the uncut section is stiffer and therefore provides a superior torque and stiffness, it is relatively short. The leakproof connection may further be facilitated with a ring, O-ring, or other leakproof connection type known in the art. An intermediate section 65 extends between proximal section 64 and distal section 66 and may be laser cut with a series of slits 78 that enable each cut section to achieve a desired bending radius. For example, intermediate section 65 includes an interrupted spiral cut (not shown) to provide flexibility to hypotube 70 without facilitating significant bending. Distal section 66 also includes laser cut slits 78 to facilitate bending in defined areas, as is described herein.

Figure 9:
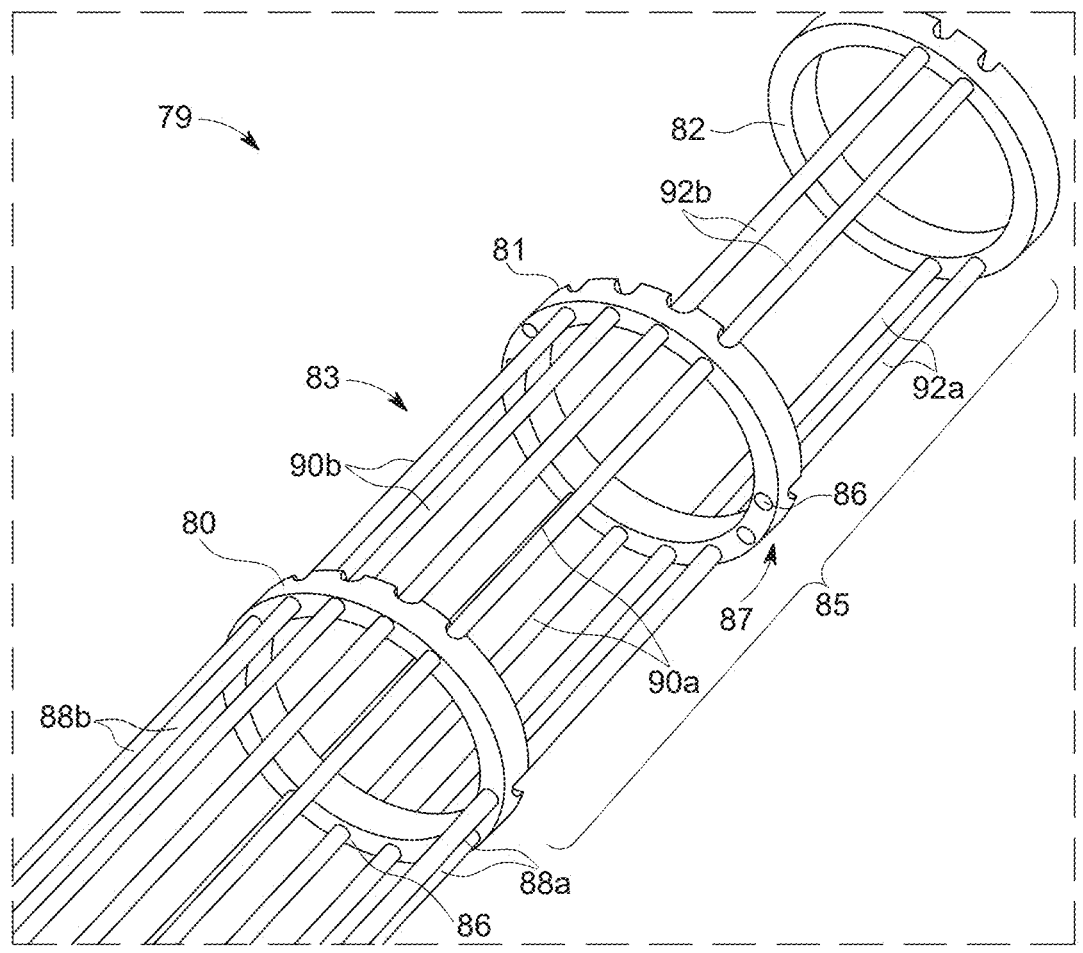
FIG. 9 is perspective view of a steering ring assembly used within the steering catheter of FIG. 6.
Figure 10:
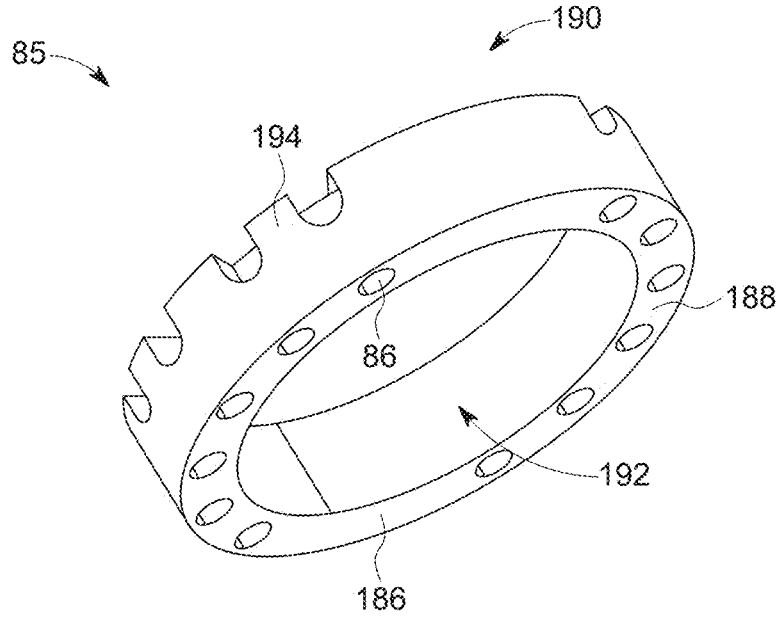
FIG. 10 is a perspective view of a steering ring, according to one embodiment.

A steering ring assembly 79, shown in FIG. 9, is provided to facilitate the steering of steering catheter 24. It should be understood that the steering ring assembly 79, as described in greater detail below, provides for three-way steering, even though the steering catheter 24 of FIG. 2 is illustrated as a two-way steering embodiment. Steering ring assembly 79 preferably has steering rings 85 including a first (e.g., proximal) ring 80, second ring 81, and third (e.g., distal) ring 82, each spaced sequentially along a proximal/distal axis of steering catheter 24. It is also contemplated that other designs, such as steering ring assembly 79 with two rings or with more than three rings are possible. Each of these components is described in further detail below.

To minimize interactions between steering catheter 24 and extension catheter 26, it is beneficial to omit all sharp edges at the distal end of steering catheter 24, especially on the inner surfaces and outer surfaces at or near the third ring 82. First ring 80 and second ring 81 sit on the outside of hypotube 70 and do not interfere with the inner components of hypotube 70, such as the extension catheter 26. The third ring 82 may be slit over the hypotube 70. A step in the ring 82 may butt up against the hypotube 70, with the step having the same inner diameter as the hypotube 70 so as to not narrow the inner lumen. A polymer layer (not shown) includes a braid or a coil and may be provided as an outer layer surrounding steering catheter 24. The polymer layer may guide each steering cable to align parallel to the axis of the steering catheter 24 and to further prevent each steering cable from moving radially outward along the longitudinal axis of steering catheter 24 between steering rings.

Steering rings 85 may be formed from stainless steel, titanium, or other materials known in the art that are capable of withstanding forces from steering cables and can be manufactured precisely to fit within steering catheter 24. Further, steering rings 85 are manufactured to have a large enough inner diameter to receive hypotube 70 and the components within hypotube 70, such as extension catheter 26. Each steering ring 85 has a plurality of lumens 86 configured to receive steering cables 83 and a central lumen 192. Lumens 86 are formed entirely through a proximal-distal direction of rings 85 and are preferably round, although different shape lumens are envisioned. Lumens 86 may be spaced adjacent to another lumen 86 in a lumen pair. For example, each lumen of the lumen pair may be spaced 10° angularly offset from the other or at another angle defined by the bending radius of the steering cable. Rings 85 extend from a proximal end 188 to a distal end 190 and define a body 186 therebetween. Lumens 86 are formed entirely through body 186.

To selectively control the curvature of steering catheter 24, the steering catheter is provided with a plurality of tension cables 83. Tension cables 83 travel distally from steering catheter handle 68 on the handle assembly 14 through a plurality of lumens in first steering ring 80 located on the outside of hypotube 70. Some of the tension cables 83 then continue to travel through a plurality of lumens of the second ring 81, and some through a plurality of lumens of the third ring 82. Each tension cable 83 acts as part of a set of two cables including a pull/tension cable and a return cable, each tension cable being configured to pull in a specific direction and each return cable being configured to pull in a generally opposite direction. Further, because each tension cable 83 is routed distally through a steering ring and then returns proximally adjacent to the distal-bound cable, each tension cable 83 has two axially extending portions, each axially extending portion extending through one of a pair of lumens within the steering rings. Thus, each ring 85 includes a plurality of lumens spaced around its circumference, preferably in pairs to receive the distal-bound tension cable portion and its adjacent proximal-bound tension cable portion. Rings 85 may include features such as a cutout and step 194 to limit the radius of curvature of tension cable 83 as it turns 180°, where the distal-bound tension cable portion turns around and transitions to the proximal-bound tension cable portion, which reduces the risk of pinching and the impact of stresses that could damage the tension cable. The routing of tension cables 83 through the respective rings in which the tension cables turn 180° may provide a secure attachment without the need to rely on welding or adhesives to make that attachment. In another embodiment, tension cables 83 may not travel through the steering catheter 24 in pairs, but rather as a single cable that attaches to a specific ring without having a separate portion of the single cable returning to the steering catheter handle. In that embodiment, the cables would continue to act as a set with a tension and return cable for pulling in generally opposite directions, but each tension cable would only have a single portion axially extending to (or through) the steering rings.

Figure 12:
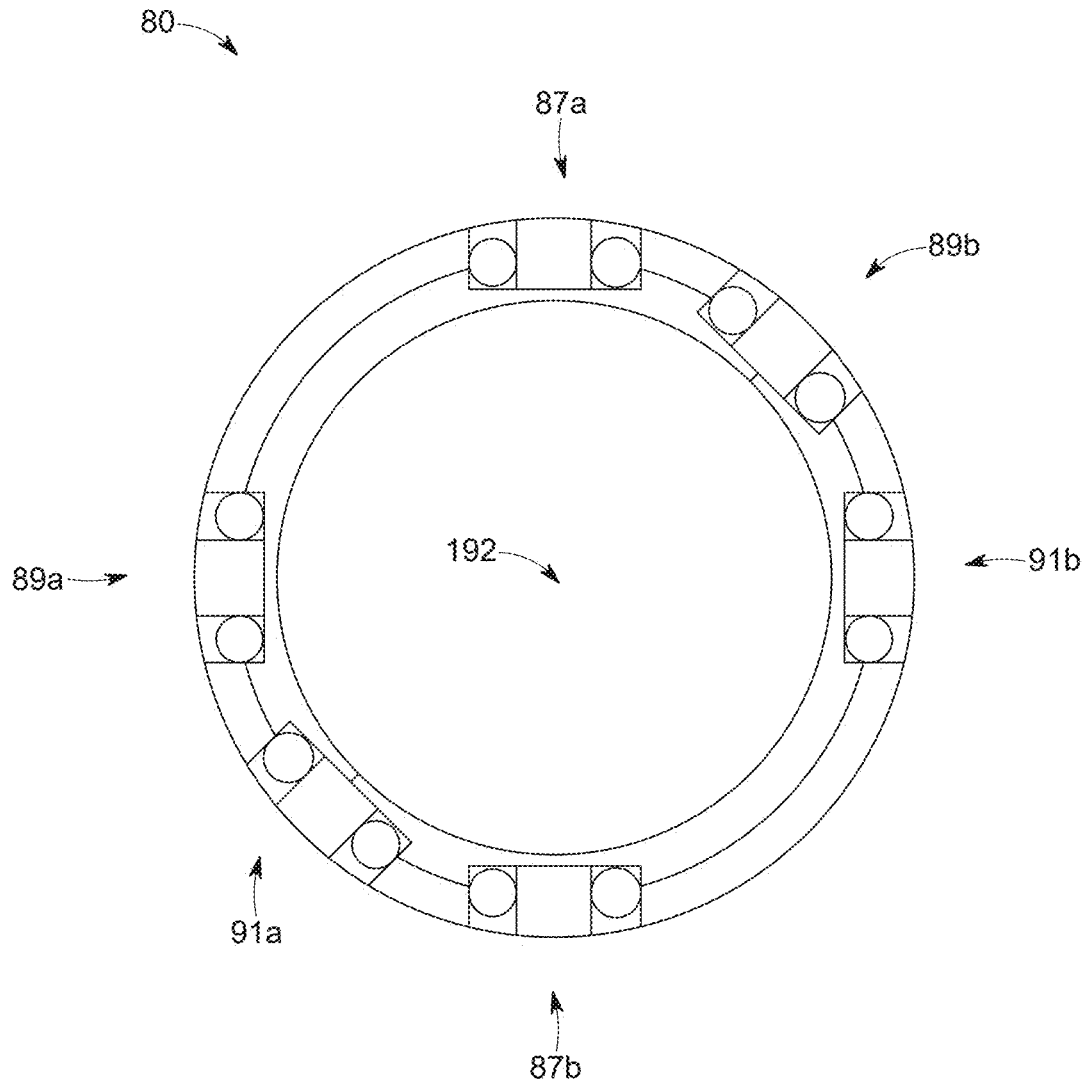
FIG. 12 is a top view of a first (e.g. proximal) steering ring of the steering ring assembly of FIG. 9.

As depicted in FIG. 9, steering ring assembly 79 includes three rings. The most proximal ring 80, shown in FIG. 12 is located closest to handle assembly 14 and has the greatest number of tension cables 83 running through it. Two of the cables provide anterior/posterior movement of the steering catheter 24 along anterior/posterior directions. Anterior/posterior cables 88a, 88b travel distally from handle assembly 14 to lumen pairs 87a, 87b within the first steering ring 80. Anterior/posterior cables 88a, 88b then turn 180° and pass through the other corresponding lumen of the lumen pair to return to handle assembly 14. Each of the lumen pairs associated with the anterior/posterior cables 88a, 88b is preferably spaced about 180° apart from each other in first steering ring 80. However, other arrangements for spacing of the lumen pairs 88a, 88b are envisioned. Thus, one of anterior/posterior cables 88a, 88b will act as a tensioning/pull cable and the other will act as a return cable to straighten the catheter after the tensioning cable has been pulled to bend the catheter in a primary desired direction.

To adjust the steering catheter 24 in an anterior or posterior direction, an operator will actuate a control of handle assembly 14 corresponding to the anterior/posterior cables 88a, 88b. For example, to turn the steering catheter 24 in an anterior direction, an operator will rotate a control knob clockwise, the control knob operably coupled to steering cables 88a, 88b through any coupling manner known in the art. This rotation will pull the anterior cable proximally toward handle assembly 14. Simultaneously, the posterior cable, preferably spaced 180° around the circumference of ring 80, will slacken and allow for additional cable length required for the outer radius of the cable bend. This combination of tension and returning steers the distal end 12 of catheter assembly 16, at ring 80, in an anterior direction.

Figure 13:
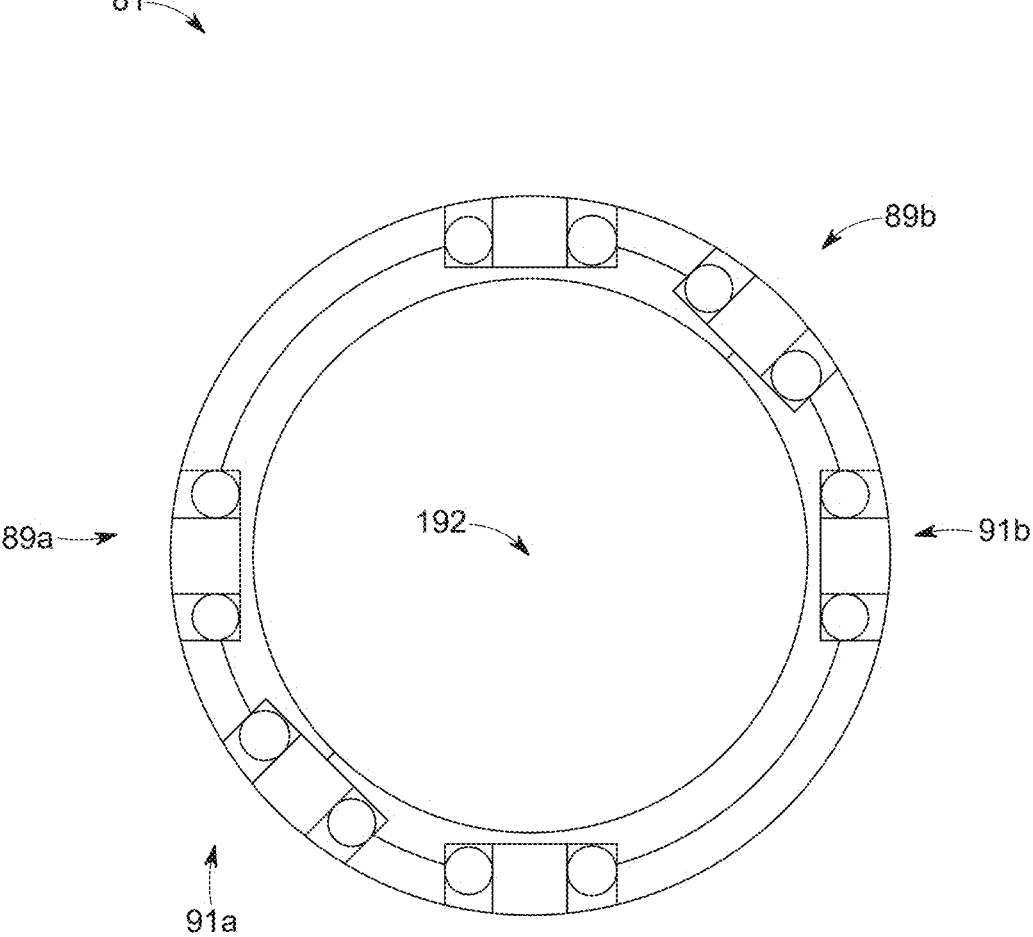
FIG. 13 is a top view of a second (e.g. middle) steering ring of the steering ring assembly of FIG. 9.

Second ring 81 may be formed substantially similarly or identically as first ring 80. Because anterior/posterior cables 88a, 88b do not extend to second ring 81, lumen pairs 87a and 87b may be left open and unused, may be plugged, or otherwise may be omitted during manufacturing second ring 81. The second ring 81 depicted in FIG. 13 shows identical lumens as first ring 80 in FIG. 12, although not all lumens are utilized in second ring 81. Second ring 81 preferably has lumens 86 in pairs 89a, 89b to receive a set of cables 92a, 92b, the tension cable of the set associated with steering in either a medial direction toward the midline of a patient's body or a lateral direction away from the midline of a patient's body, and the return cable of the set associated with steering in the opposite direction. As explained in more detail below, cable set 92a, 92b may pass through second ring 81, but may not be directly coupled to second ring 81. Second ring 81 also has lumens in pairs 91a, 91b to receive a cable set 90a, 90b, the tension cable of the set associated with raising the height of the distal end 12 of catheter assembly 16 and a corresponding return cable of the set associated with lowering the height. The height adjusting cables 90a, 90b extend distally from handle assembly 14 to second ring 81, where they turn 180° and are routed through the other lumen of the pair 91a, 91b similar to the anterior/ posterior cables 88a, 88b with first ring 80. Height adjusting cables 90a, 90b then extend proximally to handle assembly 14.

Traditional catheter steering mechanisms, such as the steering catheter depicted in FIG. 6, typically have a single set of steering cables associated with the anterior/posterior directions, and a single set of steering cables associated with medial/lateral directions. Further, traditional steering catheters typically have two distinct cut patterns in the corresponding hypotube to allow for steering in two planes of motion. This typical configuration allows for each tension cable in the anterior/posterior cable set to be located approximately 180° circumferentially from each other, and for each tension cable in the medial/lateral cable set to be located approximately 180° circumferentially from each other. For example, because anterior and posterior are opposite directions, it is generally preferably that the tension cables that control anterior and posterior steering are positioned on opposite sides (e.g., 180 degrees) of a steering ring. The same is true for medial and lateral. However, a downside of this configuration is that it does not account for a third degree of motion that has a directional component aligned with a different steering motion. For example, it may be desirable to adjust the height of the distal end 12 of catheter assembly 16, which is a medial to lateral motion, similar to the medial lateral steering. Due to the small size of the left atrium 42 and the bend that the distal end 12 of catheter assembly 16 makes to reach the native mitral valve annulus 34 (e.g., after traversing the transseptal puncture), it is beneficial for the steering catheter 22 to have a third set of tension cables 83 accounting for the height of the distal end 12 of catheter assembly 16. This height bending preferably happens in the same plane as the medial/lateral bending from the medial/lateral tension cables 92a, 92b.

Because tension cables 83 cannot be infinitesimally small in diameter and because each lumen of the lumen pair cannot be placed infinitesimally close to an adjacent pair due to manufacturing feasibility, a third pair of lumens and tension cables will inherently cause some degree of offset for the medial-to-lateral and height steering (the "height" steering also being in the medial-to-lateral direction). In other words, if a first set of tension cables controls a first medial-lateral steering, a second set of tension cables cannot also be identically positioned through the steering rings to control a second medial-lateral steering, since the first set of tension cables already occupies the desired space on the steering ring. However, the configuration of the lumens in the steering rings may be optimized for a desired outcome. For the preferred embodiment depicted in FIG. 13, each lumen pair has a lumen pair located approximately 180° across the second ring, but those diametrically opposed lumen pairs do not correspond to the same cable set. As depicted, lumen pair 89a configured to receive one cable of the set of a medial/lateral tension cables 92a, 92b is diametrically opposed from lumen pair 91b configured to receive one cable of the set of height adjusting cables 90a, 90b. Likewise, lumen pair 89b is diametrically opposed to lumen pair 91a. This configuration allows for two cable sets that each control motion in the medial/lateral direction (albeit at different points along the length of the catheter) with the only sacrifice being a slight angular offset for each cable set so that the return cable is not oriented 180° across the steering ring from the tension cable. Because the return cables experience less tension than the tensioning cables, the slight angular offset described herein will not have a negative effect on the steering maneuvers of steering catheter 24.

To adjust the height of steering catheter 24, an operator can actuate a control of handle assembly 14 corresponding to the height adjusting cables 90a, 90b. For example, to raise the height of distal end 12 of catheter assembly 16, an operator can rotate a control clockwise which will tension a cable of the height adjusting cables 90a, 90b and relax the opposite return cable. This combination of tension and relaxation controls the height of distal end 12 of catheter assembly 16 in the same plane as the medial/lateral bend, discussed below.

Figure 11:
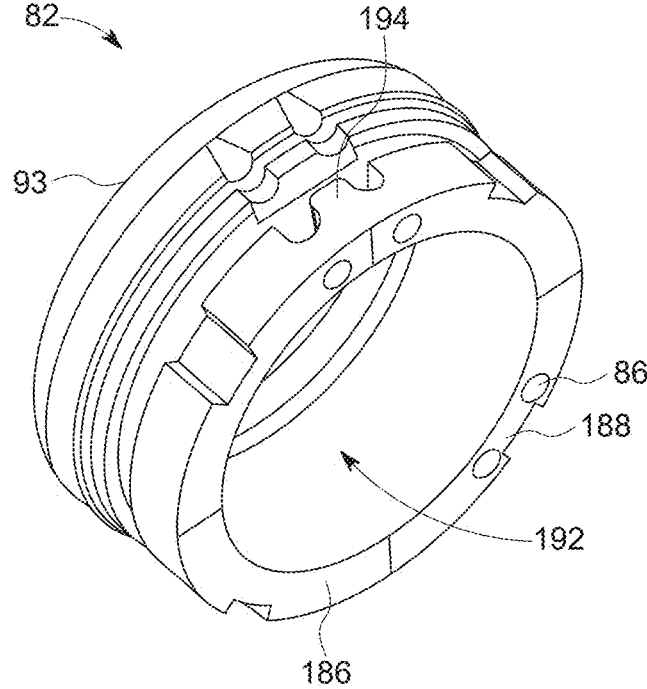
FIG. 11 is a perspective view of a distal steering ring, according to another embodiment.
Figure 14:
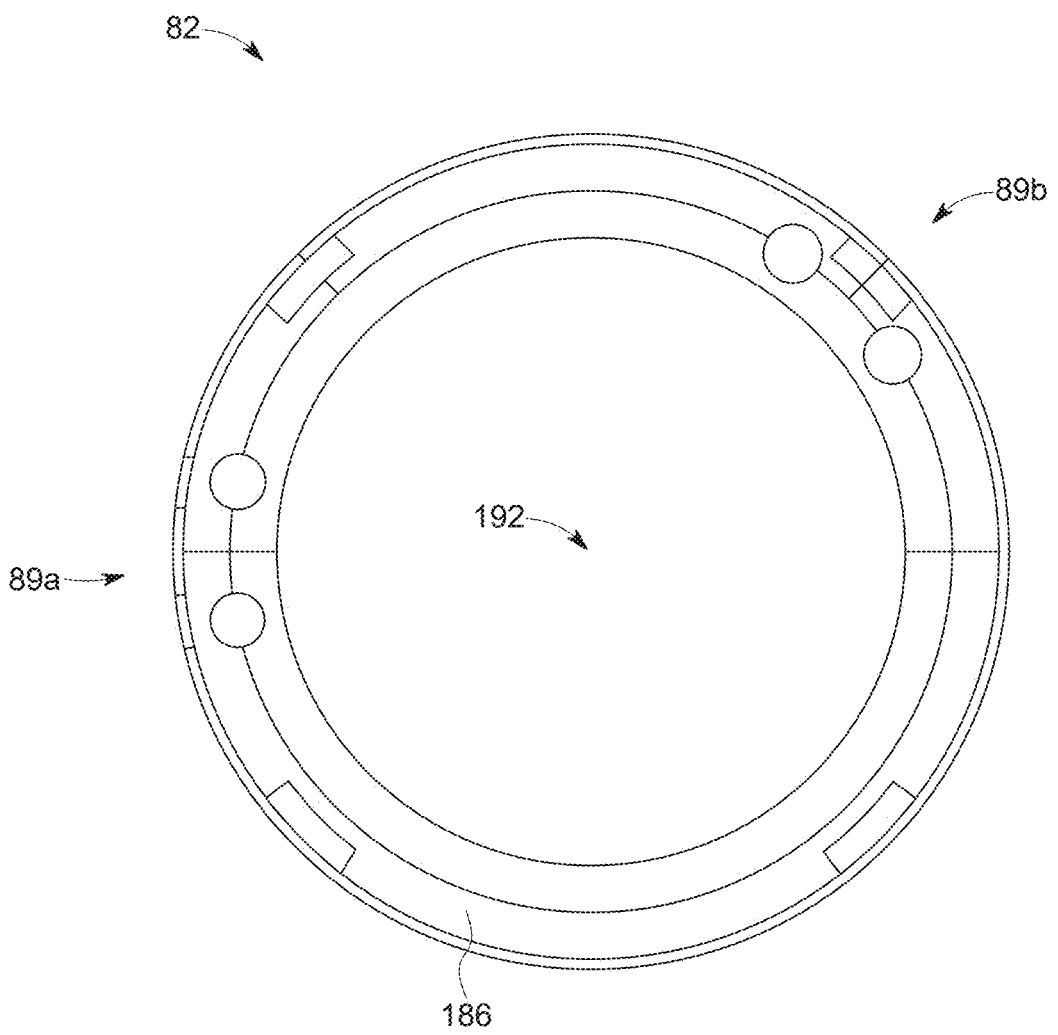
FIG. 14 is a top view of a third (e.g. distal) steering ring of the steering ring assembly of FIG. 9, according to one embodiment.

As depicted in FIGS. 11 and 14, third ring 82, also referred to as a tip ring because it is the most distal ring in steering catheter 24, may have lumens for receiving only the medial/lateral adjustment cables 92a, 92b. Alternatively, the third ring 82 may be designed in a similar manner to the first ring 80 and the second ring 81 (albeit with a smooth inner radius to allow for translation of extension catheter 26) although not all lumens will be utilized. As depicted in FIG. 14, each pair of lumens 89a, 89b for medial/lateral adjusting cables 92a, 92b is located approximately 140° apart from each other; however, other angles, such as 160°, are also envisioned. Third ring 82 may also include a ring cap 93. Ring cap 93 is substantially dome shaped to facilitate translation of steering catheter 24 through outer sheath 22 and may further include a coating to help prevent any inner component snagging on an outer component. Such a coating may also be applied to the distal section 66 of steering catheter. Ring cap 93 may be dimensioned to limit interference between outer components, such as the coil elements of the outer sheath 22. Ring cap 93 may be integrally formed with third ring 82 or it may be attached to third ring 82 via threads, fasteners, or other attachment types known in the art.

Since tension cables 83 primarily transmit a pull force, third ring 82 will be pulled proximally during steering manipulations, particularly steering manipulations of the medial/lateral adjusting cables 92a, 92b. This may stress the joint between third ring 82 and the distal section 66 of steering catheter 24. To provide a stable joint sufficient to withstand these stresses, third ring 82 may include a step 194 that forms an inner diameter on the proximal end of the ring that is substantially similar to the diameter on the distal section 66 of steering catheter 24. Steering catheter 24 may be inserted into third ring 82 such that it bears against the distal section 66 of the steering catheter 24, thereby providing support as the third ring 82 is pulled proximally.

With the distal section 66 of hypotube 70 inserted fully into third ring 82 and abutting step 194 of third ring 82, third ring 82 may be laser welded to hypotube 70 with a laser seam weld. The laser weld may be a continuous line where the inner diameter at the proximal end of third ring contacts the outer surface of steering catheter 24. A continuous seam weld may beneficially smooth out potential tolerance mismatches between the inner diameter of third ring 82 and the outer diameter at the distal section 66 of steering catheter 24. A polymer layer may be applied around steering catheter 24 and third ring 82 to produce a liquid-tight structure and impart substantial lubricity to the steering catheter.

In some embodiments, steering catheter 24 may be rotationally keyed to outer sheath 22. Outer sheath 22 may be rotationally aligned with and fixed relative to steering catheter 24 using a key and corresponding keyway feature, slots and corresponding tabs, or other rotational keying mechanism known in the art. Keying mechanisms further assist when valve cover 56 (which may be the same as the distal end 48 of the outer sheath 22) is pulled proximally over the steering catheter 26 prior to deployment. Alternatively or additionally, alignment markers may be provided at the proximal end 12 of catheter assembly 16 to visually indicate rotational alignment.

Figure 8:
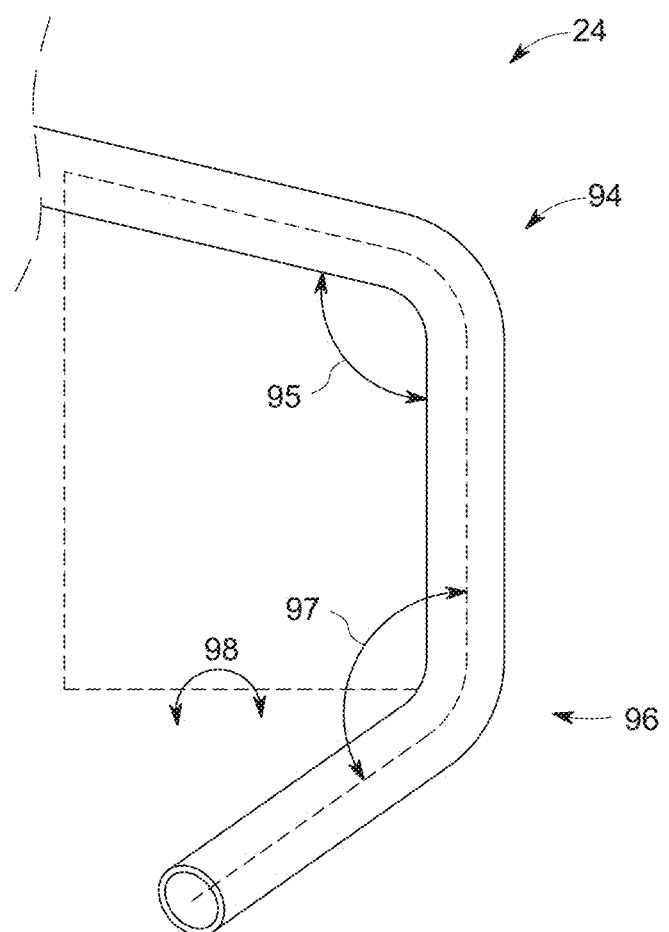
FIG. 8 is a perspective view showing the bending motions of a steering catheter having two-way steering.

FIG. 8 illustrates an example of a series of compound bends that steering catheter 24 may make during the delivery, recapture, repositioning, or retracting of a prosthetic mitral valve. It should be understood that FIG. 8 illustrates a two-way steering system (e.g. anterior-posterior and medial-lateral steering only). While accessing the mitral valve annulus 34, steering catheter 24 may be steered in at least two planes of motion (A-P and M-L) that may be substantially perpendicular to one another. In the illustrated example, steering catheter 24 has a first bend 94 with a first bend angle 95 measured between the longitudinal axis of a first portion of the steering catheter and the longitudinal axis of a second portion of the steering catheter. In some embodiments, first bend angle may be between about 40° and about 160°, more often between about 90° and about 140°, or about 130°. Steering catheter 24 also has a second bend 96 with a second bend angle 97 between a longitudinal axis of the second portion of the steering catheter and the longitudinal axis of a third portion of the steering catheter. The second bend 96 may also have a rotational angle 98 relative to a plane in which the longitudinal axis of the first and second portions of the steering catheter lie. In one embodiment, the second bend angle 97 is in a range of about 45° to about 135°, including about 60°.

FIG. 6 shows the preferred embodiment of steering catheter 24 and various cutting patterns that can be used in different sections of steering catheter 24 to produce the desired bends. For example, cut section 106 corresponds to the most distal end of steering catheter 24 between the second ring 81 and third ring 82, and bends with the flexion of medial/lateral adjust cables 92. Cut section 108 corresponds to an intermediary steering portion of steering catheter 24 between first ring 80 and second ring 81 and bends with the flexion of height adjusting cables 90. Cut section 110 corresponds to the most proximal steering portion of steering catheter 24 proximal to first ring 80 and bends with the flexion of anterior/posterior adjusting cables 88. Each ring, 80, 81, 82 is connected to the hypotube of the steering catheter in a non-slotted portion as depicted in FIG. 6.

Figure 7:
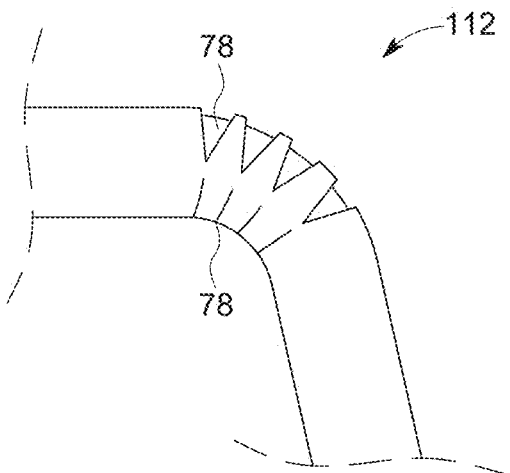
FIG. 7 is a side view of an exemplary bend of the steering catheter of FIG. 6.

Each section can include cut patterns that can include one or more slits 78 and/or island cuts and/or dogbones. Slits 78 may transmit longitudinal force along the catheter and also allow bending of the catheter when it is deflected in a direction opposite the slits. Island cuts may also be employed to allow bending of the catheter when it is deflected in the direction of the island cuts. For example, slits 78 and island cuts, when located on opposite sides of steering catheter 24, may direct preferential bending of the catheter, as shown by exemplary bend 112 in FIG. 7. Island cuts may be formed so that they progressively change in size in the length direction of steering catheter 24. For example, island cuts may progressively get smaller in the distal direction along the length of steering catheter 80. Such a cut pattern would provide a gradient bend that gradually increases in deflection at successively more proximal sections. Further, slits and/or cuts/dogbones must account for all three degrees of motion of steering catheter 24. Other size slits are also envisioned where different orientations of height adjusting cables 90a, 90b and medial/lateral adjusting cables 92a, 92b are employed within second ring 81. Slits are configured to transition from an open position to a closed position. For example, the slits in the distal cut portion 106 are configured to open when the underlying medial/lateral adjusting cable 92a, 92b is tensioned, and the opposing slits corresponding to the opposite return cable of the medial/lateral adjusting cable 92, 92b are configured to close. The same open and closed slit configurations apply to the slits in intermediary cut portion 108 and proximal cut portion 110 when the height adjusting cables 90a, 90b and anterior/posterior cables 88 are tensioned and relaxed, respectively. To accommodate the two cable sets in the medial and lateral plane, slits 78 relating to the intermediary cut portion 108 and distal cut portion 106 are preferably located on opposite sides of the hypotube.

As depicted in the preferred embodiment of FIG. 6, each of the three cut sections corresponds to a set of steering cables and steering rings and is configured to bend a certain direction. As shown, proximal cut portion 110 extends distally along a steering portion to a location where the first ring 80 is positioned. Proximal cut portion 110 is configured to bend along the anterior and posterior directions due to manipulation of the anterior/posterior cables 88a, 88b as they engage with first ring 80. Preferably, the anterior/posterior cables 88a, 88b are positioned 90 degrees from the spines in proximal cut portion 110 (or, in other words, aligned with the center of the cuts/slits) in order to maximize bending upon tensioning the corresponding anterior/posterior cables 88a, 88b. The intermediary cut portion 108 extends between the location of the first ring 80 and the location of the second ring 81 and is configured to adjust the height of the distal end of the steering catheter due to the manipulation of height adjusting cables 90a, 90b at second ring 81. It should be understood that the "height" direction is generally aligned with the medial-lateral direction. Preferably, the height adjusting cable 90a, 90b that is the "steering" or "tension" cable is aligned with the center of the cuts that allow for the desired operational bend. However, the height adjusting cable 90a, 90b that is the "return" cable is not perfectly aligned with the center of the slits that allow for the return bend (e.g. to straighten the intermediary cut portion 108) since, as described above, the height adjusting cables 90a, 90b cannot be perfectly opposite each other (assuming the height "pull" cable is already positioned perfectly opposite the medial/lateral "pull" cable). However, even if the return cable of the height adjusting cables 90a, 90b is not perfectly aligned with the slits, the slits will still tend to ensure that the return bend occurs in desired direction. This tendency is increased because less stress/force is required for the return bend compared to the steering bend. The distal cut portion 106 extends between the location of the second ring 81 and the location of the third ring 82 and is configured to adjust the distal end of the steering catheter in medial and lateral direction due to the manipulation of the medial/lateral adjusting cables 92a, 92b at third ring 82. As with the height adjusting cables 90a, 90b, preferably, the medial/lateral adjusting cable 92a, 92b that is the "steering" or "tension" cable is aligned with the center of the cuts that allow for the desired operational bend, while the medial-lateral adjusting cable 90a, 90b that is the "return" cable is not perfectly aligned with the center of the slits that allow for the return bend (e.g. to straighten the distal cut portion 106) since, as described above, the medial/lateral adjusting cables 92a, 92b cannot be perfectly opposite each other (assuming the height "pull" cable is already positioned perfectly opposite the medial/lateral "pull" cable). In other words, the cuts of the intermediary cut portion 108 that allow for the corresponding operational height bend are positioned diametrically opposed to the cuts of the distal cut portion 106 that allow for the corresponding medial/lateral operational bend, with the corresponding tensioning cables being aligned with the center of the respective cuts, while the return cables are slightly offset from the center of the slits that allow for the corresponding bending to return from the operational bends.

The distal-most section of steering catheter 24 preferably has a straight section. In the illustrated cut pattern, this may be manifest as an uncut section 114. The uncut, relatively straight portion allows the components advancing past the distal section 66 of steering catheter 24 to continue along a straight path. For example, by pointing the distal section 66 of steering catheter 24 directly at the mitral valve annulus, the components advancing distally beyond the steering catheter (such as, for example, extension catheter 26) will continue on a straight trajectory toward/through the annulus. Moving proximally from straight, uncut section 114, the bend in steering catheter 24 forms gradually before increasing to form the full bend.

To provide effective steering and positioning at the mitral annulus, the distal section 66 of hypotube 70 may be cut with a pattern that allows a bending radius of about 15 mm or less (e.g., 5 to 15 mm). The intermediate section 65 of hypotube 70 may be cut to allow a bending radius of between about 30 cm and about 45 cm. The proximal section 64 of hypotube 70 may remain uncut to ensure that the steering catheter has sufficient stiffness, torqueability and pushability to effectively operate, although as noted above, this may be mainly for purposes of sealing.

The three-way steering embodiment described above relies on a diametrically opposite pull/return cable pair for anterior/posterior steering, and two pairs of medial/lateral and height pull/return cables, where the cable pairs are not diametrically opposite because the operative medial/lateral pull cable is diametrically opposite the operative height pull cable. However, three-way steering may be achieved in other ways. For example, some or all of the return cables may be omitted. In this scenario, the pull cables are positioned exactly as described above, but return cables are simply omitted. Typically, much larger forces are needed during the operative steering than in the return steering, and thus the return cables are not always critical. In fact, as tension on a particular pull cable is released, at least some amount of return steering is expected to naturally occur.

In other embodiments, each steering direction may include a pull-return cable pair, and each cable in the pair may be diametrically opposite the other cable in the pair. In this embodiment, if the slits or cutouts are included in the configuration shown in FIG. 6, only one of the medial/lateral pull cable and height pull cable may be aligned with the center of the respective slits or cutouts. In other words, the medial/lateral pull cable may be aligned with the center of the "top" open slits in distal cut portion 106, but the height pull cable would need to angularly offset from the "bottom" open slits in the intermediate cut portion 108. Because of this angular offset, the maximum bend may not be achievable when tensioning the height pull cable. In other embodiments, the slits and cutouts in the intermediate section 108 may be angularly offset so that the centers of the slits and cutouts align with the respective pull/return height cables. But the tradeoff in this embodiment is that the intermediate section 108 will bend in a plane that is not perfectly aligned with the desired plane of bending. While these two configurations are possible and may be suitable, the above-described solution of having the medial/lateral pull cable diametrically offset from the height pull cable has been found to provide superior control compared to the other options.

FIGS. 19A-19C show a method of steering distal section 66 along a series of bends described herein to position distal section 66 at the native mitral valve annulus 34. It should be understood that, in FIG. 19A, the leading end of the delivery device is passing through the atrial septum, for example via a puncture made with a needle in a previous step, which may be followed by a balloon expansion to enlarge the hole. Generally, once the valve cover 56 containing the collapsed prosthetic heart valve therein has passed through the atrial septum, the majority of the steering may be performed. For example, the inferior vena cava is typically oriented in the up-and-down direction of FIGS. 19A-D, and not in the left-to-right direction shown in the figures. Thus, some amount of steering will be required to turn from the up-and-down inferior vena cava direction toward the atrial septum. And while steering may be performed in any order and combination desired, one exemplary sequence of steering is described below. First, an operator may manipulate the medial/lateral cables 92a, 92b to try to turn the distal section 66 and valve cover 56 approximately 90° toward or into the native mitral valve annulus 34. Typically, this includes medial steering and thus medial steering may be the operating bend and lateral steering may be the return bend. Looking to FIG. 6, the open slits 78 (at the top of the figure) of cut section 106 may begin to close to bend cut section 106 toward or into the mitral valve annulus 34. Next, with the valve cover 56 within in or near the mitral valve annulus, an operator may manipulate the anterior/posterior cables 88a, 88b to swing the valve cover 56 anteriorly or posteriorly, to attempt to generally align the valve cover 56 with the native mitral valve in the anterior-posterior direction. As described above, because the anterior/posterior cables 88a, 88b are positioned about 180 degrees apart from each other, tensioning the anterior/posterior cables 88a, 88b may result in movement of the valve cover 56 anteriorly or posteriorly within a single plane. When the valve cover 56 is substantially parallel to the longitudinal axis of the mitral valve annulus 34, it may be advanced distally using extension catheter 26 until the valve cover 56 is actually within the mitral valve annulus 34. However, it may be difficult to achieve the correct height of the system, which may be a position in which about ⅓ of the length of the valve cover 56 is above the mitral valve annulus and about ⅔ of the length of the valve cover 56 is below the mitral valve annulus. However, in some systems, the optimal positioning may require less depth than the ⅓ vs. ⅔ depth described above. For example, the height of the valve cover relative to the annulus may be dependent on the height of the septal puncture and thus the height at which the valve cover 56 crosses the septum. The particular height at which the septal crossing occurs may be limited by a patient's anatomy, and in many situations, the septal crossing may not be able to be performed at the desired height, which may result in the valve cover 56 being too shallow or too deep with respect to the mitral valve annulus. If the valve cover 56 is too shallow, the extension catheter (if an extension catheter is included) may be used to advance distally. However, it is far more frequent that the valve cover 56 may be too deep through the mitral valve annulus. This may make it difficult or impossible to deploy the prosthetic heart valve in the desired position. However, as is described in more detail below, the third steering direction allows for an increase in height, if needed, to correct an overly-deep position of the valve cover 56. And if an extension catheter is not included and the initial positioning is too shallow, the third steering direction allows for a decrease in height to compensate for the initial undesirable positioning.

FIG. 19B illustrates the valve cove 56 after the initial medial/lateral and anterior/posterior steering operations.

Although not shown to scale, the positioning shown in FIG. 19B may be determined to be too deep beyond the mitral valve annulus and within the left ventricle. If such a determination nis made, the operator may manipulate the height adjusting cables 90a, 90b to raise the height of the distal end of the catheter toward the top of the left atrium 42, as shown in FIG. 19C. In particular, looking to FIG. 6, the open slits of cut section 108 (at the bottom of the figure) may begin to close by tensioning the desired height adjusting cable 90a or 90b, causing both cut section 108 and cut section 106 to effectively hinge upwardly relative to the proximal cut section 110. As shown in FIG. 19C, this height change may create more clearance relative to the mitral valve annulus 34, but may also cause the valve cover 56 to lose the desired orientation relative to the mitral valve annulus 34. Thus, after increasing the height as shown in FIG. 19C, the medial/lateral cables 92a, 92b may again need to be actuated to again bend the cut section 108 toward parallel alignment with the mitral valve annulus 34, as shown in FIG. 19D. However, due to the earlier height manipulation, it can be seen in FIG. 19D that the valve cover 56 has a shallower position than the initial positioning of FIG. 19B. It should be understood that manipulation of the medial/lateral cables 92a, 92b and the height adjusting cables 90a, 90b may be performed sequentially or at the same time as desired. It should also be understood that the exact positions of the valve cover 56 relative to the mitral valve annulus shown in FIGS. 19A-D may not be reflective of actual desired positions within a procedure in terms of depth/shallowness of the valve cover 56—but are rather intended to show how the height may be adjusted (in this case, adjusting to a more shallow position) by using the third steering direction.

Still referring to FIG. 19D, the extension catheter 26 may be advanced to move the valve cover 56 into position for valve deployment in systems which include an extension catheter. However, in systems without an extension catheter, the valve cover 56 may be withdrawn to begin to deploy the valve once the valve cover 56 is at the desired position and height relative to the mitral valve. And, as described directly below and in connection with FIG. 20, after the ventricular flange of the prosthetic heart valve has been deployed within the left ventricle 41, the extension catheter 26 may be retracted to "pull" the ventricular flange into engagement with tissue at the native valve annulus on the ventricle side. However, in systems in which an extension catheter is omitted, the deployment may proceed without the additional step of "pulling" the ventricular flange proximally toward the mitral valve annulus. It should be understood that the placement of the medial/lateral cables 92a, 92b and height adjusting cables 90a, 90b within the steering ring assembly is preferably such that the cable that is to be tensioned to steer the valve cover 56 medially (e.g. between the position shown in FIGS. 19C to 19D), and that the cable that is to be tensioned to increase the height of the valve cover 56 (e.g. between the position shown in FIGS. 19B and 19C) are positioned 180 degrees offset from each other and aligned with the slits that open and close to facilitate the bending. This medial steering and height increase may each be thought of as the more "important" of the pair of medial/lateral and height adjustment steering capabilities, respectively. Thus, these two steering motions are highly precise and each within the same plane as each other, just in opposite directions. On the other hand, after valve implantation, when the catheter needs to be generally straightened for removal, the lateral steering and height decrease steering may each be slightly out of the desired plane of action. In other words, the lateral steering cable and height decrease cable, which are offset about 180 degrees from each other, are also slightly offset from the medial/lateral plane. This may result in less precise steering, but because these two steering directions are less important to be precise, it is an acceptable tradeoff for having the more important medial and height increase steering mechanisms be highly precise.

Figure 15:
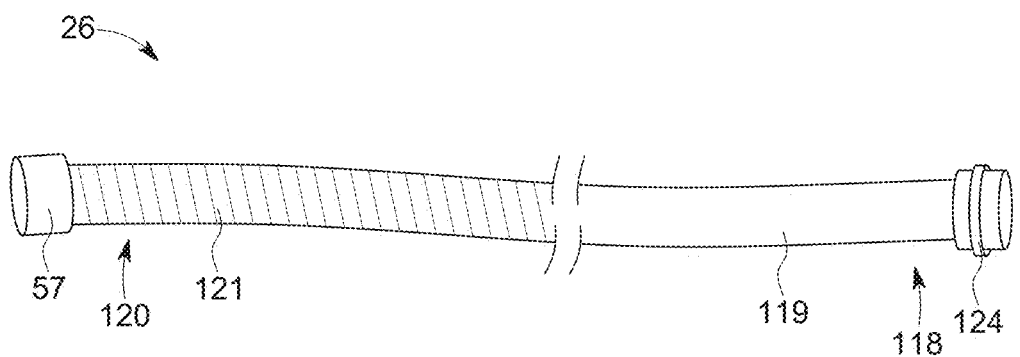
FIG. 15 is a side view of the extension catheter of FIG. 1.

FIG. 15 depicts the extension catheter 26. As noted above, the extension catheter 26 is optional, and may be entirely omitted in embodiments of the delivery system. If included, the extension catheter 26 is concentrically nested within steering catheter 24. Extension catheter 26 may withstand relatively high compression forces during the deployment of a prosthetic heart valve. For example, during the release of prosthetic mitral valve 20 by the retraction of outer sheath 22, the countervailing compression force on extension catheter 26 may be on the order of about 100 lbs., although in other embodiments on the order of between about 15 lbs. and about 30 lbs. Extension catheter 26 preferably has sufficient flexibility to allow for proper deflection and curvature to obtain a desired position in the mitral valve annulus. A coil structure, such as the coil structure in a distal section of outer sheath 22, is beneficial because it has enough flexibility and is also able to withstand high compression forces. In some embodiments, the coil may be a flat wire coil, which has been found to provide effective balance between flexibility and compressive strength.

Extension catheter 26 extends from a proximal end 118 to a distal end 120, with a proximal section 119 adjacent the proximal end and a distal section 121 adjacent the distal end. Proximal section 119 of extension catheter 26 may be formed from a stainless steel hypotube having a laser cut interrupted spiral pattern of slits beginning at a spaced distance from proximal end 118, with a seal 124 comprising an O-ring at the proximal end for forming a fluid-tight seal at the connection of the extension catheter to handle assembly 14. The distal section 121 of extension catheter 26 may be formed with a tri-coiled structure. That is, distal section 121 may be formed with three layers of wire coils, with the inner and outer layers being wound in the same direction, and the middle layer being wound in a direction opposite that of the inner and outer layers. The three coils are coextensive and are welded to one another at their ends, as well as welded to proximal section 119. The tri-coil structure provides distal section 121 with enough flexibility to navigate the tortuous path to the patient's mitral valve annulus and at the same time reduces the compression of the distal section as it effectively pushes the prosthetic mitral valve out of catheter assembly 16. As a result, extension catheter 26 is better able to maintain the position of the prosthetic mitral valve relative to the native mitral annulus as catheter assembly 16 is manipulated to deploy the prosthetic valve.

Extension catheter 26 may include a can structure 57 laser welded to distal end. Can 57 is configured to constrain and hold at least a proximal section of the prosthetic mitral valve, which may help portions of the valve frame in line with the retracting force without starting to bow outwardly.

The length of can 57 may be sufficient to aid in maintaining coaxial alignment of the distal end 120 of extension catheter 26 with catheter assembly 16 to avoid or minimize unwanted tilting. For example, can 57 preferably has a length to diameter ratio of greater than or equal to 1, though in alternative embodiments the ratio may be smaller, such as about 0.25 to 1, depending on the stiffness of distal section 121. Can 57 also provides an effective structural surface to act as a counterforce to maintain the prosthetic heart valve in a proper pre-deployed position when outer sheath 22 is retracted. In some embodiments, one or more edge portions of can 57 may include a taper and/or smooth surface for easier sliding of the can within outer sheath 22. An outer groove around the circumference of can 57 may include a wire formed from tantalum or other highly radiopaque and/or echogenic material to identify the end of extension catheter 26 under x-rays or ultrasound imaging, even while the can is within valve cover 56.

Figure 16:
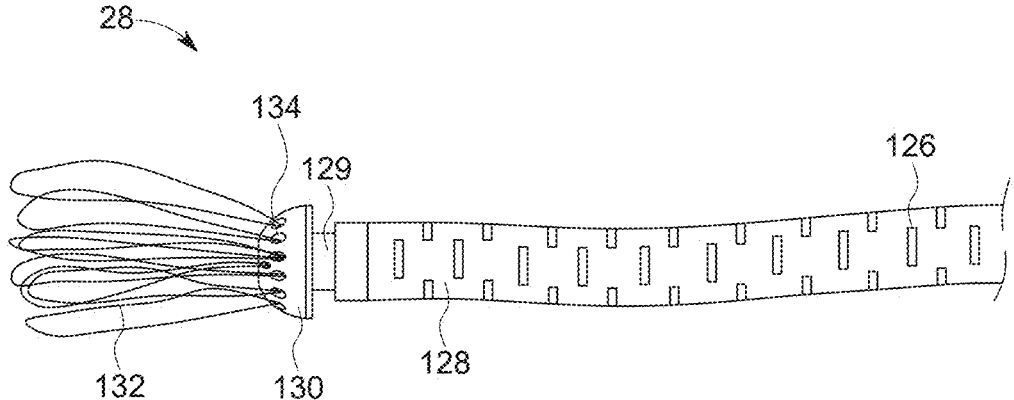
FIG. 16 is a side view of a distal section of the suture catheter of FIG. 1.

FIG. 16 shows suture catheter 28. Suture catheter 28 may be concentrically nested within extension catheter 26. Generally, suture catheter 28 is flexible to follow the tortuous path to the patient's heart, with a very flexible distal end that can accommodate the deflections of steering catheter 24. In addition, suture catheter 28 is capable of withstanding substantial tension during the loading of the prosthetic mitral valve into valve cover 56 and should maintain axial tension on the prosthetic mitral valve prior to deployment. By maintaining such axial tension, suture catheter 28 may aid in maintaining the proximal portion of the prosthetic valve within can 57 and the position of the prosthetic valve within catheter assembly 16, as will be described further below.

Suture catheter 28 may be formed from a stainless steel hypotube having an interrupted spiral pattern of slits laser cut along its length to provide flexibility. A proximal suture ring 129 may be laser welded to the distal end 128 of suture catheter 28. Proximal suture ring 129 may be internally threaded to mate with the external threads of a distal suture ring 130. A plurality of suture loops 132 connected to distal suture ring 130 may releasably connect to attachment features on the prosthetic mitral valve. As a result, as suture catheter 28 is retracted relative to outer sheath 22, tension will be applied through distal suture ring 130 and suture loops 132 to the prosthetic mitral valve, drawing it into can 57 and valve cover 56.

Figure 17:
FIG. 17 is a perspective view of the nosecone catheter of FIG. 1.

FIG. 17 depicts a nosecone catheter 30. Nosecone catheter 30 is concentrically nested within the lumen of suture catheter 28. It is beneficial for each of the components of catheter assembly 16 to be able to slide relative to one another under various challenging curvatures to which the catheter assembly is subjected during a transseptal approach to the mitral valve annulus. Accordingly, it is beneficial for nosecone catheter 30 to be able to translate freely within suture catheter 28.

Providing a smooth inner surface within suture catheter 28 to facilitate the translation of nosecone catheter 30 therein can be challenging. In particular, in preferred embodiments in which suture catheter 28 comprises a laser cut hypotube, it can be challenging to achieve a smooth inner surface. For example, the laser cut hypotube may be too small/tight to enable sufficient electro-polishing. While honing is another option, the length of the laser cut portion of the hypotube makes such procedure difficult. Other techniques, such as extrude honing, may not produce the desired smoothness on the inner lumen of steering catheter 24.

An alternate embodiment of a suture catheter 28 having improved smoothness on its inner walls is provided herein. Suture catheter 28 has a relatively long proximal portion that is formed from a stainless steel hypotube having a proximal end, a distal end, and an interrupted spiral pattern of slits laser cut along its length. Suture catheter 28 also has a relatively short distal portion formed from a length of hypotube having a proximal end, a distal end, and a pattern of dog bone slits laser cut along its length. A thin-walled stainless steel spacer tube is laser welded at one end to the distal end of the proximal portion of suture catheter 28, and laser welded at its other end to the proximal end of the distal portion of the suture catheter, joining the proximal portion to the distal portion so that there is a space therebetween. A proximal suture ring having internal threads for mating engagement with distal suture ring may be laser welded to the distal end of the distal portion of suture catheter 28. A free-floating polytetrafluoroethylene tube may line the lumen of distal portion from spacer tube to proximal suture ring, covering any sharp edges and weld lines resulting from the assembly of the components. In addition, a fluorinated ethylene propylene tubing may be heat shrunk around the outside of proximal portion, spacer tube, and distal portion to provide a leakproof seal around suture catheter 28.

Distal suture ring 130 is connectable to the proximal suture ring 129 of the suture catheter 28. A preferred distal suture ring 130 for use with catheter assembly 16 is described in U.S. Provisional Application No. 63/228,269, the disclosure of which is hereby incorporated by reference herein. Distal suture ring 130 extends in a longitudinal direction between a distal end and a proximal end and has somewhat of a mushroom shape with a generally cylindrical body at the proximal end terminating in an enlarged head with a domed or hemispherical surface at the distal end. A lumen may extend in the longitudinal direction through the cylindrical body and head of distal suture ring 130 and may be sized to receive a guidewire and a nosecone catheter therethrough. As illustrated, cylindrical body may be formed with external threads sized and shaped to securely connect to the internal threads in the proximal suture ring 129 of suture catheter 28. However, other mechanisms for fastening distal suture ring 130 to suture catheter 28 are also contemplated so long as they are sufficiently strong to withstand the substantial tensile forces that will be exerted thereon as prosthetic heart valve 20 is collapsed and loaded into valve cover 56.

The head of distal suture ring 130 may have a diameter that is substantially larger than the diameter of cylindrical body, thereby defining a shoulder extending around the cylindrical body and facing toward the proximal end of the coupling ring. A plurality of round apertures or bores 134 may extend through head from shoulder to surface. Bores 134 may extend parallel to one another and parallel to the longitudinal direction of distal suture ring 130, and each has a diameter sized to receive a length of suture thread. One or more suture loops 132 may be attached to the head of distal suture ring 130. Suture threads 132 may be formed of various materials, both man-made and natural. Examples of natural suture materials may include, but are not limited to, silk, linen, and catgut. Examples of synthetic suture materials may include, but are not limited to, textiles such as nylon or polyester, or flexible metallic cables.

Referring to FIG. 16, an elongated suture thread may be threaded through a plurality of the bores 134 in distal suture ring 130 to form suture loops 132. A plurality of knots may be formed in suture loops 132 to secure the suture loops 132 to distal suture ring 130. Knots may also prevent adjacent lengths of suture thread from separating too far from one another to create a large loop or lasso that may potentially become entangled with the prosthetic heart valve as it is being deployed. Suture loops 132 are intended to hook onto the pins of prosthetic heart valve 20 and to apply tension to assist in collapsing the prosthetic heart valve during loading into valve cover 56, as described more fully below. A radiopaque marker may be provided on each of suture loops 132 to help visualize the locations of suture loops 132, and in particular the positions of suture loops 132, during the deployment of prosthetic heart valve 20 in a patient The innermost component of catheter assembly 16, nosecone catheter 30, is positioned within the lumen of suture catheter 28 and has a lumen therethrough configured to receive guidewire 32. For example, the lumen of nosecone catheter 30 may have a diameter of about 0.037 inches so as to be compatible with a standard 0.035-inch guidewire, although other sizes may be utilized according to particular application needs. Nosecone catheter 30 extends from a proximal end 31 to a distal end 33. A proximal portion of nosecone catheter 30 is formed from a very thin-walled stainless steel hypotube that, because of its small diameter, is flexible. Adjacent distal end 33, nosecone catheter 30 has a distal portion that includes 2-3 concentric layers of coiled wire laser welded to the hypotube of the proximal portion. The coiled structure of the distal portion provides much greater flexibility than that of the proximal portion, enabling nosecone catheter 30 to form tight bends within the restricted confines of the heart. The innermost coil of the distal portion is wound in a first direction and the overlying coil is wound in the opposite direction. As a result, when nosecone catheter 30 is rotated in one direction, the coils in the outer layer will tighten, such that the torque applied at the proximal end 31 of the nosecone catheter will be transmitted all the way to the distal end 33. The torque will not be transmitted to distal end 33, however, when nosecone catheter 30 is rotated in the opposite direction. If it is desired to be able to transmit torque in two directions along the entire length of nosecone catheter 30, three coil layers are necessary, with the third coil layer being wound in the direction opposite that of the underlying coil layer (i.e., in the same direction as the innermost coil). The distal portion of nosecone catheter 30 may also include a stainless steel tube adapter laser welded to the free ends of the coils. The tube adapter is externally threaded at its distal end for attachment of a nosecone 136. By making nosecone 136 detachable from nosecone catheter 30, prosthetic heart valve 20 can be loaded into a fully assembled catheter assembly 16, including nosecone catheter 30. That is, the distal end 33 of nosecone catheter 30 can be inserted through prosthetic heart valve 20 during the loading procedure, without having to slide the prosthetic heart valve over the entire length of the nosecone catheter from its proximal end 31.

Embodiments of nosecone 136 that may be used with delivery system 10 are described in detail in U.S. Patent Publication No. 2020/0323634, the disclosure of which is hereby incorporated by reference herein. One such embodiment of nosecone 136 that is connectable to nosecone catheter 30 is illustrated in FIG. 17. Nosecone 136 provides an angled, atraumatic shape which assists in advancing catheter assembly 16 through the patient's vasculature and inter-atrial septum 40 to mitral valve annulus 34, all while minimizing damage to the vasculature and cardiac tissue. Nosecone 136 may be injection molded from a relatively soft polymeric material, such as polyurethane, mixed with a foaming agent, such as Foamazol® available from Bergen International LLC. The foaming agent may create small voids within nosecone which enable the nosecone to be visible under ultrasound imaging. The voids also reduce the mass of nosecone 136, facilitating the injection molding process. The polymeric material used to form nosecone 136 may also incorporate a radiopaque material, such as barium sulfate, whereby the nosecone produces a ghost-like image that is visible under x-rays. Following injection molding, nosecone 136 may be coated with a hydrophilic coating.

Nosecone 136 may be molded around a rigid polymer insert. The insert may be completely encased by the softer polymer forming nosecone 136 and may include an elongated shaft 138 surrounded coaxially by a rim 140. Rim 140 may be connected to shaft 138 by a plurality of spokes that space the rim from the shaft and orient the rim in a plane that is perpendicular to the longitudinal axis of the shaft. Shaft 138 may have a lumen (not shown) extending through the entire length thereof in alignment with a bore (not shown) in the distal end of nosecone 136. The diameters of the lumen and the bore are such that guidewire 32 can be inserted in sliding relationship therethrough. At its proximal end, shaft 138 may include internal threads sized to mate with the threads on a tube adapter to assemble nosecone 136 to nosecone catheter 30. In that regard, the proximal end of nosecone 136 has an enlarged bore with a diameter sized to receive the tube adapter of nosecone catheter 30 therein. Rim 140 may include a groove along its outer circumference. The groove may be adapted to receive a radiopaque and/or echogenic material, such as a tantalum wire, so that the position and orientation of rim 140 is clearly visible under x-rays and/or ultrasound.

As noted, nosecone catheter 30 and nosecone 136 have lumens or bores therein that are configured to slidably receive guidewire 32. Guidewire 32 is a thin wire that is used to guide catheter assembly 16 from the insertion site in the patient to the mitral valve annulus 34 at which the prosthetic mitral valve is to be deployed. To enable catheter assembly 16 to track all the way to mitral valve annulus 34, it may be preferable for the distal tip of guidewire 32 to be advanced into a left ventricle. Guidewire 32 preferably is highly flexible and kink-resistant in order to accommodate the tight turns encountered while advancing from the femoral vein, through septum 40 and mitral valve annulus 34, to the left ventricle 41.

Figure 18:
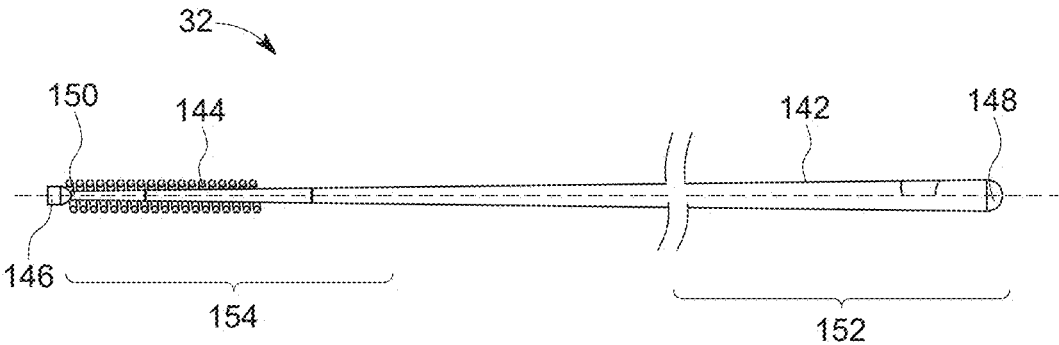
FIG. 18 is a side view of the guidewire of FIG. 1.

One embodiment of a guidewire 32 for use with catheter assembly 16 is shown in FIG. 18 and described in U.S. Patent Publication No. 2020/0155803, the disclosure of which is hereby incorporated by reference herein. Guidewire 32 includes a core wire 140 that extends from a proximal end 148 to a distal end 150. Core wire 140 has a first section 150 with a generally uniform or constant diameter closest to proximal end 148, and a second section 154 closest to its distal end 150. Second section 154 may gradually decrease or taper in diameter towards distal tip 146. A distal portion of section 154 may include a coil 144 coupled to core wire 140, and the distal end of the core wire may optionally include an atraumatic tip.

Core wire 146 may be formed of a superelastic material, such as nitinol, providing guidewire 32 with a high degree of flexibility. Coil 144 may be formed from a radiopaque and/or echogenic metal, such as tantalum, platinum, platinum iridium, gold, silver, etc., so that the distal end 150 of guide wire 32 is visible under x-rays and/or ultrasound imaging. A distal portion of second section 154 of guidewire 32, including coil 144, may have a pigtail shape, although the pigtail shape is not shown in FIG. 18. The curved configuration of the pigtail shape may prevent guidewire 32 from damaging cardiac or other tissue as it is advanced to left ventricle 41.

Guidewire 32 may be covered by an outer sleeve (not shown). In some embodiments, the entire length of core wire 142, including coil 144, may be covered by the outer sleeve. In other embodiments, the outer sleeve may cover the length of core wire 142 up to but not including coil 144. The outer sleeve may be formed of a polymeric material (e.g. shrink tube), such as a polytetrafluoroethylene tube that is applied over core wire 144 and shrunk by the application of heat. The outer sleeve imparts substantial lubricity and low surface friction to guidewire 32, enabling the guidewire to easily slide within nosecone catheter 30.

Guidewire 32 preferably has a length that is about twice the length of catheter assembly 16. Thus, for a catheter assembly that is about six feet (183 cm) long, guidewire 32 may have a length of about twelve feet (365 cm). In other embodiments, guidewire 32 may have a length of between about six feet (183 cm) and about fifteen feet (457 cm). The maximum diameter of guidewire 32, including the outer sleeve, may be between about 0.014 in. and about 0.037 in. For example, guidewire 32 may have a diameter of about 0.014 in., about 0.018 in. or about 0.035 in.

Although the particular nested configuration shown in FIG. 2 and described above represents one preferred embodiment for the various components of catheter assembly 16, alternative embodiments may include a different concentric arrangement of constituent parts. For example, some embodiments may combine steering catheter 24 and outer sheath 22 into one component and/or configure the outer sheath with steering functionality, some embodiments may include more than one catheter with steering functionality, etc.

Figure 21:
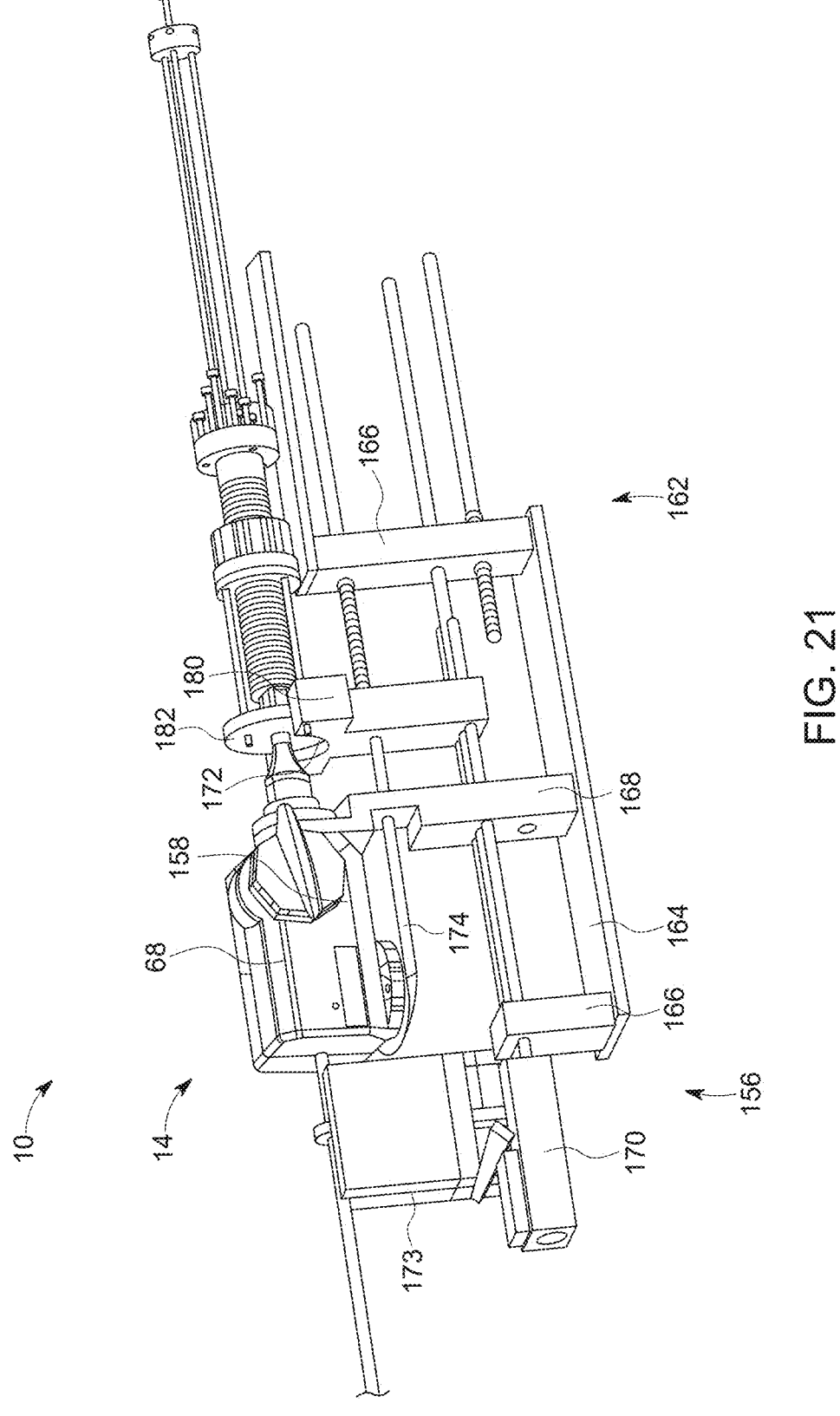
FIG. 21 is a perspective view of a delivery device for the catheter of FIG. 1.

As mentioned previously, catheter assembly 16 is connected at its proximal end to handle assembly 14, which consists of steering catheter handle 68 and a series of end rings, caps and other structures, each of which is connected at or near the proximal end of one of the components of catheter assembly 16. The proximal end 156 of steering catheter 24 is fixedly connected to the housing 158 of steering catheter handle 68. Steering catheter handle 68 includes one or more controls to which the proximal free ends of tension cables 83 are connected. For example, steering catheter handle 68 may include three controls, such as three knobs, levers, buttons, or the like, each control operably coupled to one of the three sets of steering cables. Manipulation of the controls adjusts the tension in tension cables 83 to deflect or straighten the distal section 66 (and, in some embodiments, the intermediate section) of steering catheter 24. Manipulation of one control may deflect the distal section 66 of steering catheter 24 in a first plane, such as the anterior/posterior plane, and manipulation of another control may deflect the distal section of the steering catheter in a second plane orthogonal to the first plane. Manipulation of another control may deflect the distal section 66 of steering catheter 24 in the second plane. Each control relating to steering the distal end 66 of steering catheter 24 in the second can correlate to either the medial/lateral direction or the height, as described herein. Hence, controls can be adjusted in unison to position the distal end 12 of catheter assembly 16 and valve cover 56 at a desired position and orientation relative to mitral valve annulus 34. Although the controls are shown in FIGS. 1 and 21 as knobs, alternative embodiments may additionally or alternatively include one or more buttons, sliders, ratcheting mechanisms, or other suitable controls capable of adjusting the tension in tension cables 83 to provide steering. Illustrative structures that can be used as part of steering catheter handle 68 and/or steering catheter 24 are described in U.S. Pat. No. 7,736,388, the disclosure of which is hereby incorporated by reference herein. Since steering catheter 24 is positioned within outer sheath 22, deflection of the steering catheter causes a corresponding deflection/steering of the outer sheath. A steering catheter hemostasis valve may be connected to the proximal end of steering catheter 24 just proximally of steering catheter handle 68.

Outer sheath 22 is assembled over steering catheter 24 and extends from its distal end 48 to its proximal end 46, which may be connected to an outer sheath hemostasis valve spaced distally of steering catheter handle 68. This positioning enables outer sheath 22 to be advanced distally relative to steering catheter 24 and retracted proximally relative to the steering catheter until the hemostasis valve abuts steering catheter handle 68.

Extension catheter 26 extends proximally through steering catheter 24 and steering catheter handle 68 where its proximal end 118 is fixedly coupled to an extension catheter holder 182 positioned proximally of the steering catheter handle. Extension catheter holder 182 may be in the form of a disk having a central aperture (not shown) that enables suture catheter 28 to extend proximally therethrough. A flush port may be positioned on the rim of extension catheter holder 182 allows for flushing the interior of extension catheter 26.

Suture catheter 28 extends proximally through extension catheter 26, steering catheter handle 68, and extension catheter holder 182 and is fixedly coupled at its proximal end 126 to a suture catheter control 160 positioned proximally of extension catheter holder 182. Suture catheter control 160 may be in the form of a disk or puck having a central aperture (not shown) through which nosecone catheter 30 may extend proximally. A flush port may be positioned on the rim of suture catheter control 160 allows for flushing the interior of suture catheter 28.

Nosecone catheter 30 extends proximally from nosecone 136 through suture catheter 28, steering catheter handle 68, extension catheter holder 182, and suture catheter control 160 and is coupled to a nosecone catheter control (not shown). Nosecone catheter control is in the form of a disk or puck to which a proximal portion of nosecone catheter 30 is fixedly attached. A central aperture (not shown) through nosecone catheter control enables the proximal end of nosecone catheter 30 and guidewire 32 to extend proximally of the nosecone catheter control. Although both suture catheter control 160 and nosecone catheter control have been described as disks or pucks, they may have different shapes, including spheres, ovoids, polygons or other shapes that may be grasped and translated. In addition, the shape of suture catheter control 160 may be the same as or different than the shape of nosecone catheter control.

Both suture catheter control 160 and nosecone catheter control may be selectively locked in longitudinal positions relative to extension catheter holder 182 or may be released so that the suture catheter control is translatable proximally and distally relative to extension catheter holder 182 and the nosecone catheter control, and the nosecone catheter control is translatable proximally and distally relative to extension catheter holder 182 and the suture catheter control. In order to maintain the axial alignment of suture catheter control 160 and the nosecone catheter control with extension catheter holder 182 (and also the axial and rotational alignment of the components of catheter assembly 16), both the suture catheter control and the nosecone catheter control may translate along a plurality of rigid alignment rods of housing 158. Each alignment rod is connected at its distal end to extension catheter holder 182 and extends proximally therefrom through one plurality of apertures in suture catheter control 160 and another plurality of apertures in the nosecone catheter control. An enlarged fitting on the free end of each alignment rod prevents the nosecone catheter control and suture catheter control 160 from being removed from the rods.

In one embodiment, suture catheter control 160 may include a release mechanism and nosecone catheter control may include a release mechanism (not shown). The release mechanisms may interact with a threaded rod that is fixedly connected at its distal end to extension catheter holder 182 and that extends proximally through apertures (not shown)

in suture catheter control 160 and the nosecone catheter control. The release mechanisms may each include an end piece engageable with a threaded rod. A pin may be connected at one end (such as by threaded engagement) to the end piece and may be connected at an opposite end (such as by threaded engagement) to a pushbutton. A spring mounted on the pin between the end piece and the pushbutton may bias the end piece into engagement with the threaded rod.

The engagement with the threaded rod prevents suture catheter control 160 from translating proximally or distally relative to extension catheter holder 182 and the nosecone catheter control. Depressing the pushbutton to disengage the release mechanism from threaded rod frees suture catheter control 160 to translate along the threaded rod either proximally or distally relative to extension catheter holder 182 and nosecone catheter control. Once suture catheter control 160 is in the desired position, releasing release mechanism will again bias the end piece into engagement with the threaded rod, locking the suture catheter control in a fixed longitudinal position relative to the threaded rod. Moving suture catheter control 160 proximally or distally relative to the nosecone catheter control will selectively translate suture catheter 28 relative to nosecone catheter 30, nosecone 136 and the other components of catheter assembly 16. A set screw on the rim of suture catheter control 136 opposite the end piece may be screwed inwardly to prevent the pushbutton from being depressed, thereby locking the suture catheter control in a fixed longitudinal position on the threaded rod. The use of the set screw is intended to prevent the inadvertent actuation of the release mechanism and translation of suture catheter 28. Although the use of a threaded rod is shown, handle assembly 14 may include a rod having other structures (grooves, divots, depressions, etc.) for engaging with the end piece of the release mechanisms and when in the engaged position.

Similarly, the release mechanism may be biased into engagement with the threaded rod within nosecone catheter control. This engagement prevents nosecone catheter control from translating proximally or distally relative to extension catheter holder 182 and suture catheter control 160. Depressing the pushbutton disengages the release mechanism from the threaded rod, freeing the nosecone catheter control to translate along the threaded rod either proximally or distally relative to extension catheter holder 182 and suture catheter control 160. Moving the nosecone catheter control proximally or distally relative to suture catheter control 160 will selectively translate nosecone catheter 30 and nosecone 136 relative to suture catheter 28 and the other components of catheter assembly 16. Once the nosecone catheter control is in the desired position, releasing the release mechanism will again bias it into engagement with the threaded rod, locking the nosecone catheter control in a fixed longitudinal position relative to the threaded rod. Although a spring-loaded pin such as shown has been found to provide effective and rapid actuation, other mechanisms for quickly disengaging from the threaded rod may additionally or alternatively be utilized, such as a toggle release, snap shackle, quick-release skewer, and/or set screw, for example.

The ability to the retract nosecone 136 relative to suture catheter 28 reduces the risk that the nosecone will become overextended during deployment, where it could become tangled in chordae tendineae and/or cause injury to cardiac tissue. For example, during the deployment of a prosthetic mitral valve, suture catheter 28 may be advanced to disengage from the prosthetic valve. If nosecone 136 is not retracted relative to the advancing suture catheter 28, the nosecone could extend too far into the ventricle where it could catch chordae tendineae and/or impinge against the cardiac wall. Additionally, the independent movement of nosecone catheter 30 (with nosecone 136) allows the gap between the nosecone and valve cover 56 to be closed following the deployment of the prosthetic mitral valve. When the prosthetic mitral valve has been released, nosecone 136 is separated from valve cover 56 by a distance, such as by about 40 mm. To avoid drawing air into catheter assembly 16, the gap between valve cover 56 and nosecone 136 may be closed by drawing the nosecone towards the valve cover, preferably in the left side of the heart to avoid sucking air into the catheter assembly when pulled back into the right side of the heart (where there is relatively low pressure).

Referring to FIG. 21, delivery system 10 is supported by a stabilizer 162 including a base 164 and a plurality of rigid supports 166. A handle support 168 is fixedly connected to base 164 and extends upward to a semi-circular cradle that supports a disk-shaped member connected to the proximal end of steering catheter handle 132. A cover may be assembled to the cradle over the disk-shaped member to secure the disk-shaped member and steering catheter handle 132 to the handle support 168. A support 166 is also fixedly connected to base 164 and extends upward therefrom to a height lower than that of handle support 168. An extension catheter support 180 between handle support 168 and support 166, however, is spaced above and translatable relative to base 164. The extension catheter support 180 extends upward to a semi-circular cradle 172 having a recess sized and shaped to receive extension catheter holder 182. A cover may be assembled to cradle 172 over the extension catheter holder 182 to secure extension catheter holder 182 in its assembled position.

An outer sheath support (now shown) is fixedly mounted to a slider block 170 near the distal end of base 164 and extends upward to a semi-circular cradle 173 sized to receive outer sheath 22. Cradle 173 has a width sized to be received between two rings spaced from one another around the exterior of outer sheath 22. The engagement of cradle 173 between the rings prevents outer sheath 22 from translating proximally or distally relative to the outer sheath support. A cover may be assembled to the outer sheath support over outer sheath 22 to secure the outer sheath in its assembled position. Slider block 170 is positioned within a channel in the top surface of a slider block. Slider block 170 may be formed from anodized aluminum or another lightweight material, while the slider block guide may be formed from polytetrafluoroethylene or another low friction material so that the slider block slides smoothly and easily on the slider block guide. A pair of arms fixedly connected to the opposite sides of support 166 and handle support 168 also connect to opposite sides of the slider block guide and support the slider block guide below slider block 170. As will be explained below, slider block 170 may slide in the slider block guide distally and proximally relative to base 164 and delivery system 10 mounted thereon.

Base 164 may be slidably mounted to a portable table. The table may include a platform supported by a plurality of height-adjustable legs. A second platform may be hingedly connected to the first platform so that the proximal end of the second platform can be raised or lowered relative to the first platform, which may orient the delivery system 10 at a transverse angle to horizontal. A lock may secure the second platform at a desired angular orientation relative to the first platform. The second platform may have side rails that are undercut to define a pair of slots that extend the length of the second platform. The slots are sized to receive the longitudinal edges of base 164, enabling the base to slide proximally and distally relative to the second platform and the table.

Stabilizer 162 also includes a plurality of actuators that selectively control the translation of base 164 and the translation of the components of catheter assembly 16 relative to one another. A base actuator may include a threaded rod 174 that is engaged with internal threads in support 166 and an extension catheter support 180. At its proximal end, threaded rod 174 is coupled to a support post 166 fixedly attached to a second platform. The coupling of threaded rod 174 to support post 166 is such that the threaded rod is rotatable but not translatable relative to support post 166. An actuating knob may be affixed to the proximal end of threaded rod 174. Rotating the actuating knob in one direction will cause base 164 and all of the components assembled to the base to advance distally relative to the second platform and the table, while rotating the actuating knob in the opposite direction will cause the base and the components assembled to the base to retract proximally relative to the second platform and the table. Also, since threaded rod 174 is threadedly engaged with both support 166 and extension catheter support 180, the distance between support 166 and extension catheter support 180 will remain fixed as base 164 translates proximally or distally.

An outer sheath actuator includes a threaded rod that is supported for rotation through handle support 168, extension catheter support 180, and support 166. The distal end of the threaded rod is engaged with internal threads in a slider block 170, and an actuating knob is affixed to its proximal end. Threaded rod is freely translatable through handle support 168 and support 166, while a collar or other structure on the threaded rod fixes the threaded rod to extension catheter support 180 so that the threaded rod rotates in but does not translate relative to extension catheter support 180 as it translates relative to the other supports. As a result, while extension catheter support 180 is held in a fixed position (as explained below), rotation of an actuating knob in one direction causes slider block 170 to translate proximally, retracting outer sheath 22 relative to the other components of catheter assembly 16. Rotation of the actuator knob in the opposite direction causes slider block 170 to translate distally, advancing outer sheath 22 relative to the other components of catheter assembly 16. A pair of smooth, rigid rods may extend from slider block 170 proximally through apertures in handle support 168, extension catheter support 180, and support 166 to maintain the alignment of the outer sheath support with the other portions of delivery system 10 as they translate relative to one another. The retraction of outer sheath 22 may be utilized to deploy a prosthetic heart valve sheathed at or otherwise attached to the distal end of the outer sheath, while the advancement of the outer sheath over the prosthetic heart valve may be utilized to recapture the valve.

Stabilizer 162 also includes a deployment actuator that translates several of the components of catheter assembly 16 relative to steering catheter 80. The deployment actuator includes a threaded rod that is supported for rotation at its distal end in handle support 168, extends through extension catheter support 180, and is supported for rotation at its proximal end in support 166. The deployment actuator is fixed to handle support 168 and support 166 so that it does not translate relative to those supports as it is rotated. However, the threaded rod is threadedly engaged with internal threads in extension catheter support 180. As noted previously, extension catheter holder 182 is captured in the cradle 172 in extension catheter support 180, preventing extension catheter holder 182 from translating proximally or distally relative to extension catheter support 180. Similarly, steering catheter handle 68 is supported by handle support 168, which is held in a fixed position on base 164. As a result of this arrangement, rotation of an actuating knob on the proximal end of the deployment actuator results in the translation of extension catheter support 180 relative to handle support 168 and support 166. However, when the deployment actuator is not rotated, the threaded engagement of the deployment actuator with handle support 168, the extension catheter support 180 and support 166 holds the extension catheter support in a fixed position and prevents it from translating.

In view of the forgoing connections among the various components, the rotation of the deployment actuator in a first direction to translate extension catheter support 180 simultaneously causes slider block 170, extension catheter holder 182, suture catheter control 160, and the nosecone catheter control to retract proximally, while the position of steering catheter handle 68 remains fixed. Rotation of the deployment actuator in the opposite direction causes the advancement in the distal direction of slider block 170, extension catheter holder 182, suture catheter control 160, and the nosecone catheter control, again without translating steering catheter handle 68.

As explained above, suture catheter control 160 may be translated proximally or distally relative to the other components of catheter assembly 16 by depressing release a mechanism and manually sliding the suture catheter control proximally or distally. Translation of suture catheter control 160 causes the simultaneous translation of suture catheter 28 relative to outer sheath 22, steering catheter 80, extension catheter 26, nosecone catheter 30 and nosecone 136. As will be explained below, the proximal retraction of suture catheter 28 relative to outer sheath 22 increases the axial tension on suture loops 132 connected to the prosthetic mitral valve to maintain the prosthetic valve in a pre-deployed position within delivery system 10, while the distal advancement of the suture catheter relative to the outer sheath releases the axial tension on the suture loops and allows deployment of the prosthetic valve.

Similarly, the nosecone catheter control may be translated proximally or distally relative to the other components of catheter assembly 16 by depressing the release mechanism and manually sliding the nosecone catheter control proximally or distally. Translation of nosecone catheter control causes the simultaneous translation of nosecone catheter 30 and nosecone 136 relative to outer sheath 22, steering catheter 80, extension catheter 26 and suture catheter 28.

The following will describe the loading of prosthetic mitral valve 20 into the valve cover 56 of delivery system 10. To begin, nosecone 136 is removed from nosecone catheter 30 and the various components of catheter assembly 16 are flushed to remove air from the system. Flushing is accomplished by attaching flush lines to the outer sheath hemostasis valve, steering catheter hemostasis valve, extension catheter flush port, suture catheter flush port, and to a hemostasis valve (not shown) attached to the proximal end of nosecone catheter 30 and flowing heparinized saline through these components both individually and collectively until all or substantially all air bubbles have been removed therefrom. Vibration may be applied to catheter assembly 16 to facilitate the removal of air from the system. Procedures may also be followed to flush the distal end of catheter assembly 16 by flowing heparinized saline into valve cover 56 using a plug with a luer fitting inserted into the open end of the valve cover. To confirm proper deairing, after the plug has been removed from valve cover 56, steering catheter 80 should be advanced until its distal end is exposed beyond the distal end of valve cover 56, extension catheter 26 should be advanced until its distal end is exposed beyond the distal end of the steering catheter, suture catheter 28 should be advanced until its distal end is exposed beyond the distal end of the extension catheter, nosecone catheter 30 should be advanced until its distal end is exposed beyond the distal end of the suture catheter, all while these portions are submerged in a saline bath. Any air bubbles evident on any of these components should be removed using conventional techniques. Methods for flushing catheter assembly 16 are described in U.S. Patent Publication No. 2018/0126095, the disclosure of which is hereby incorporated by reference herein.

Following the deairing procedure, the components of catheter assembly 16 should be positioned for the loading of prosthetic mitral valve 20 into valve cover 56. To do this, nosecone catheter 30 is retracted until its distal end is just within suture catheter 28, the suture catheter and the nosecone catheter are retracted together until their distal ends are within the can 57 at the distal end of extension catheter 26 and the extension catheter is retracted until can 57 contacts the distal end of steering catheter 80. Outer sheath 22 may then be advanced until can 57 is positioned near the midpoint of valve cover 56. A loading tube (not shown) may then be assembled over outer sheath 22 so that it extends from the outer sheath support to the distal end of the valve cover 56. With the distal end of valve cover 56 protruding from the loading tube, a tantalum ring is removed from the valve cover and a loading funnel is assembled to the valve cover. The loading funnel is formed from titanium and has a cylindrical body with a lumen therethrough and a flange on both ends of the body. Internal threads at the proximal end of loading funnel mate with the external threads at the distal end of valve cover 56, enabling the loading funnel to be screwed onto the end of the valve cover. An elongated window in the body of the loading funnel enables the user to see the interior of the loading funnel as prosthetic mitral valve 20 is retracted into and through the loading funnel.

Subsequently, suture catheter 28 may be advanced by depressing the release mechanism and translating suture catheter control 160 distally. The outer sheath actuator may then be rotated to fully retract outer sheath 22 proximally, exposing the distal end of suture catheter 28 distally of the loading funnel. The loading tube may then be adjusted to increase its length until one end of the loading tube presses against the flange at the proximal end of the loading funnel and the other end of the loading tube presses against the outer sheath support, thereby applying tension to outer sheath 22. Prior to attaching prosthetic mitral valve 20 to suture catheter 28, the cuff of the prosthetic valve may be pleated inwardly to facilitate the retraction of the prosthetic valve into valve cover 56 and prevent the cuff from becoming damaged as the prosthetic valve is retracted. With the distal end of suture catheter 28 exposed beyond the end of the loading funnel, and with the loading funnel and prosthetic mitral valve assembly submerged within a saline bath, the mitral valve assembly may be assembled to the suture catheter. The prosthetic mitral valve assembly includes a distal suture ring attached to prosthetic mitral valve by a plurality of tethers, with a packaging assembly securing the prosthetic mitral valve and distal suture ring so that the tethers are tensioned. Details of prosthetic mitral valve assembly are shown and described in U.S. patent application Ser. No. 17/317,377, filed May 11, 2021, the disclosure of which is hereby incorporated by reference herein. The entire prosthetic mitral valve assembly is attached to suture catheter 28 by screwing the distal suture ring to the proximal suture ring at the distal end of the suture catheter. The release mechanism may again be depressed and suture catheter control 160 may be retracted proximally to retract suture catheter 28 and the prosthetic mitral valve assembly until the atrial petals of prosthetic mitral valve 20 are within the lumen of loading funnel. The packaging assembly may then be removed from prosthetic mitral valve 20.

At this juncture, the release mechanism may be depressed and the nosecone catheter control may be advanced distally to advance nosecone catheter 30 through prosthetic mitral valve 20 until it is exposed distally of the valve. In an embodiment where a balloon is utilized to release a prosthetic heart valve 20, a thin, elongated balloon mounted on a hypotube that is internally threaded at its proximal end may then be inflated with saline and secured by threaded engagement to the distal end of nosecone catheter 30 may be provided. A balloon mandrel (not shown) having an enlarged distal end (larger than the inner diameter of the hypotube) may be inserted longitudinally through the hypotube and nosecone catheter 30 until it protrudes from the proximal end of the nosecone catheter, with the enlarged distal end contacting the distal end of the hypotube. A clamp (not shown) may then be applied to the proximal end of the balloon mandrel. Together, the contact of the enlarged distal end of the balloon mandrel with the distal end of the hypotube and the clamp attached to the proximal end of the balloon mandrel prevent the balloon from being squeezed out distally as prosthetic mitral valve 20 is collapsed and retracted into a loading funnel.

With the balloon attached to nosecone catheter 30, the release mechanism may again be depressed and the nosecone catheter control may be retracted proximally to retract the balloon to a position within prosthetic mitral valve 20. A threaded rod may then be rotated to retract suture catheter 28 and nosecone catheter 30 together relative to extension catheter 26, steering catheter 80 and outer sheath 22, drawing prosthetic mitral valve 20 completely into the loading funnel. The balloon may then be deflated and suture catheter 28 and nosecone catheter 30 may continue to be retracted until the tips of the atrial petals of prosthetic mitral valve 20 are positioned in the can 57 at the distal end of extension catheter 26, as visible through the window in the loading funnel. Subsequently, outer sheath 22 may be advanced distally through the rotation of the outer sheath actuator until prosthetic mitral valve 20 is fully positioned in valve cover 56.

The balloon, the balloon clamp, the balloon mandrel, and the loading tube may then be removed from the components of catheter assembly 16, the loading funnel may be removed from valve cover 56 and the tantalum ring may be threaded onto the distal end of the valve cover. Nosecone catheter 30 may then be advanced distally by depressing the release mechanism and translating the nosecone catheter control so that nosecone 136 may be threaded onto the distal end of the nosecone catheter. Nosecone catheter 30 may then be retracted through operation of the nosecone catheter control until nosecone 136 seats against the distal end of valve cover 56. Delivery system 10 is now ready for delivering prosthetic mitral valve 20 into the left atrium 42 of the patient and deploying the prosthetic valve in mitral valve annulus 34.

In a conventional procedure, an incision is made in the patient's groin to access the femoral vein, and a guidewire 32 is a fed up through the femoral vein, advanced through the inferior vena cava 36 to the right atrium 38, through a puncture in intra-atrial septum 40 and into the left atrium 42. Catheter assembly 16 is then advanced over guidewire 32 until nosecone 136 is located in left atrium 42 confronting the mitral valve annulus 34. In an embodiment using an inflation balloon, the balloon may be inflated around valve cover, as described above. The balloon may be visualized with ultrasound imaging.

FIG. 20 schematically illustrate the deployment and release of prosthetic mitral valve 20 at the mitral annulus 34. Once catheter assembly 16 is properly positioned, nosecone 136 is advanced distally relative to outer sheath 22 and valve cover 56 by depressing the release mechanism and the translating nosecone catheter control distally. Nosecone 136 is advanced by an amount that provides sufficient space for the deployment of prosthetic mitral valve 20. Once the distal end 12 of catheter assembly 16 is in position at mitral annulus 34, with valve cover 56 positioned so that the inflated balloon is aligned within the annulus, a distal portion of prosthetic mitral valve 20 is positioned on the ventricular side of the annulus, and a proximal portion of the prosthetic mitral valve is positioned on the atrial side of the annulus. Outer sheath 22 and valve cover 56 may then be partially retracted by rotation of the outer sheath actuator, enabling a ventricular anchor 178 of prosthetic mitral valve 20 to be released and expand within left ventricle 41. Following the release and expansion of ventricular anchor 178, prosthetic mitral valve 20 may be retracted proximally to bring the ventricular anchor into contact against the ventricular side of mitral annulus 34. This may be accomplished by rotating the deployment actuator to retract extension catheter 26 and suture catheter 28 or, alternatively, by rotating the base actuator to retract the entire catheter assembly 16. As explained above, in order to retract extension catheter 26, enough clearance may have had to have been created in order to allow the extension catheter 26 to first be advanced.

Outer sheath 22 and valve cover 56 may be further retracted by operation of outer the sheath actuator to uncover and release an atrial anchor 176 of prosthetic mitral valve 20 on the atrial side of mitral annulus 34. At this point, prosthetic mitral valve 20 may still be held by suture loops 132 in a not yet fully deployed condition. This enables prosthetic mitral valve 20 to be further positioned or recaptured if necessary. Suture catheter 28 may then be advanced distally by depressing the corresponding release mechanism and translating suture catheter control 160 distally to relieve the tension in suture loops 132, enabling atrial anchor 176 to expand and release from the can 57 of extension catheter 26. In this regard, the distance between suture catheter control 160 (in its pre-deployed position) and extension catheter holder 182 enables suture catheter 28 to move distally a sufficient distance to reliably cause suture loops 132 to move forward, invert, slide off hooks and detach from the atrial anchor. The longitudinal position of nosecone 136 relative to suture catheter 28 can be adjusted as needed while the suture catheter is being advanced. Upon its expansion, the atrial anchor will contact the atrial side of mitral annulus 34, thus sandwiching the mitral annulus and securing prosthetic mitral valve 20 in place. The ability to rapidly actuate and translate suture catheter control 160 enables atrial anchor 176 to be deployed quickly and prosthetic mitral valve 20 to begin operating quickly, restoring blood flow from left atrium 42 to left ventricle 41. After prosthetic mitral valve 21 has been detached from suture catheter 28, the suture catheter may be retracted by again depressing the corresponding release mechanism and translating suture catheter control 160 proximally away from extension catheter holder

182, pulling suture loops 132 back into extension catheter 26. Nosecone catheter 30 may then be retracted by depressing release the corresponding release mechanism and translating the nosecone catheter control proximally until nosecone 136 is seated against the distal end of valve cover 56. Subsequently, in an embodiment with a balloon, the balloon may be deflated, which in turn collapses a fill tube, and then catheter assembly 16 may be removed from the patient.

During the deployment of prosthetic mitral valve 20, situations may arise in which it becomes desirable to resheathe the prosthetic valve and either reposition it or remove it entirely from the patient. This may occur when prosthetic mitral valve 20 is not properly positioned or not properly oriented in the native mitral annulus, or when the deployed prosthetic valve has been damaged or is otherwise not functioning as intended. During a resheathing procedure, however, substantial compressive forces are exerted on outer sheath 22 as prosthetic mitral valve 20 is collapsed and retracted into valve cover 56 or as the outer sheath is advanced to push the valve cover over the prosthetic valve. For example, when prosthetic mitral valve 20 is first loaded into valve cover 56, the loading is carried out at room temperature (below the transition temperature of nitinol where nitinol is more flexible) and with the use of loading a funnel. Even under these conditions, the loading force generated could be about 50-100 lbs. or more. During resheathing in the body (without a loading funnel and above the transition temperature of nitinol), on the other hand, the loading forces generated could be around three times higher. To achieve these forces at the distal end 12 of catheter assembly 16 can be very challenging as the catheter assembly is up to 6 ft. long and its distal end is deflected in at least two planes. Although the coil/braid portion 52/54 at the distal end of outer sheath 22 provides flexibility while permitting deployment of prosthetic mitral valve 20, that structure does not provide sufficient compressive strength for resheathing. As compressive forces are exerted on the coil/braid portion 52/54 during resheathing, the large gaps between adjacent coils will collapse, causing a foreshortening of the coil/braid portion by 50%-70% or more as the individual coils contact one another. Since braided sleeve 54 is fixedly connected at both ends to coiled layer 52, the braided sleeve must shorten by the same amount, which is either impossible or will cause the sleeve to enlarge in diameter substantially.

The foregoing arrangement facilitates the re-sheathing of a deployed or partially deployed prosthetic heart valve by decoupling the unsheathing and re-sheathing forces. During a re-sheathing procedure, the collapsing of braided sleeve 54 around coiled layer 52 prevents the individual coils from becoming offset from one another such that the full compressive force from the advancement of the hypotube can be transmitted through the coiled layer to valve cover 56, enabling the valve cover to collapse and cover the prosthetic valve. In a different embodiment, the alignment of the coils in coiled layer 52 may be maintained by a series of filaments threaded through each of the individual coils from the proximal end of the coiled layer to its distal end.

Much of the above disclosure focuses on systems and methods that allow for a particular deployment sequence of the prosthetic heart valve 20 in which the ventricular anchor 178 or flange is first deployed in the left ventricle 41, and then pulled into contact with the native annulus tissue before deploying the atrial anchor 176 or flange in the left atrium 42. However, in some circumstances, it may be desirable to deploy the atrial anchor 176 first in the left atrium 42 and then deploy the ventricular anchor 178 in the left ventricle 41. For example, one potential reason to reverse the deployment sequence is to avoid engaging the subvalvular apparatus until the end of the deployment sequence.

Figure 22A:
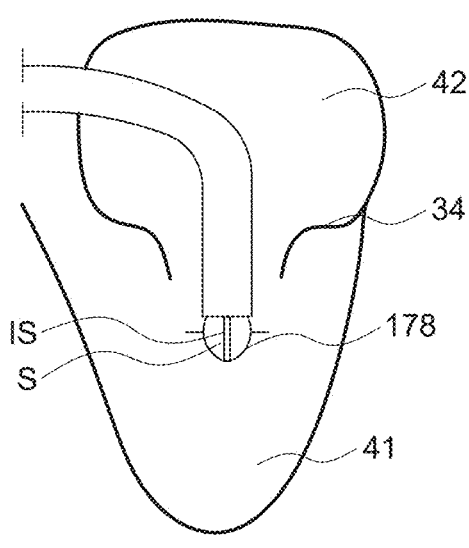
FIGS. 22A-E illustrate an alternate deployment mechanism and sequence in which the atrial anchor of the prosthetic heart valve is deployed prior to the ventricular anchor.
Figure 22B:
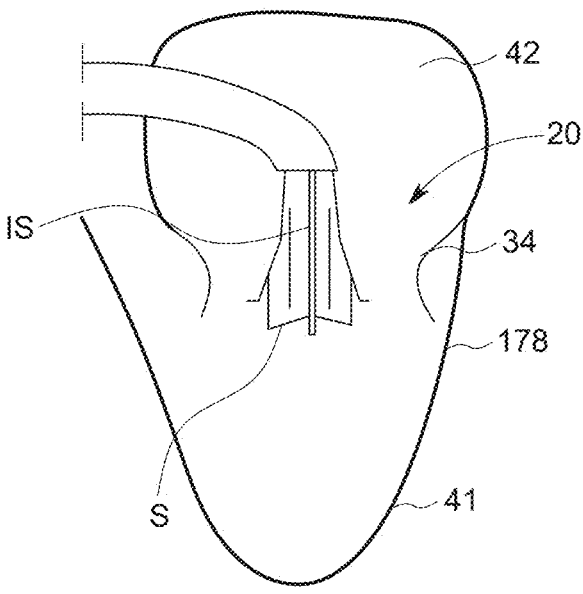

FIGS. 22A-E illustrate an alternate deployment sequence described above. For example, with the distal end of the delivery catheter in the final desired position within the mitral valve annulus 34, the valve cover (not separately identified in FIGS. 22A-E) may be retracted to expose the ventricular anchor 178 on the ventricular side of the mitral valve annulus 34. As shown in FIG. 22B, the valve cover may be further retracted to expose more of the prosthetic heart valve 20. Importantly, however, in this embodiment, despite the ventricular anchor 178 being exposed, it does not self-expand or otherwise deploy upon initial exposure. This may be accomplished by a variety of mechanisms. In the illustrated embodiment, an interior shaft IS extends through the inside of the prosthetic heart valve 20, and one or more sutures S or other wires or strings may couple the interior shaft IS to the ventricular anchor 178. For example, sutures S may be looped through or otherwise releasably connected to the ventricular anchor 178 and extend through the interior of the delivery device to a handle or other portion of the delivery device accessible to the operator outside the body. The sutures S may be kept in a configuration in which they are in tension, pulling the ventricular 178 radially inwardly toward the internal shaft IS to prevent full deployment. It should be understood that, upon withdrawal of the valve cover shown between FIGS. 22A-B, the ventricular anchor 178 may undergo slight expansion, but the sutures S connecting the internal shaft IS to the ventricular anchor 178, at least temporarily, prevent full deployment/expansion of the ventricular anchor 178.

Figure 22C:
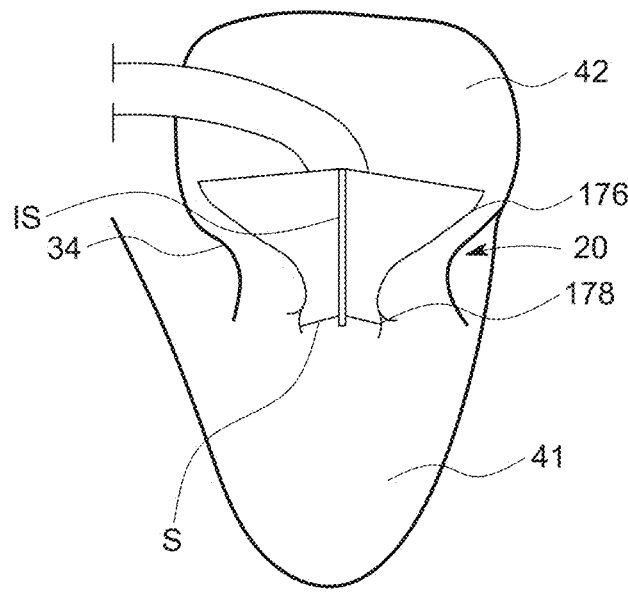
Figure 22D:
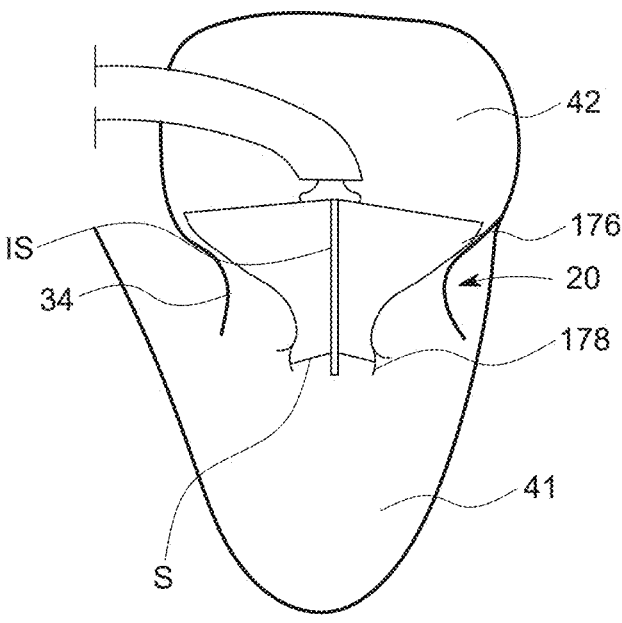
Figure 22E:
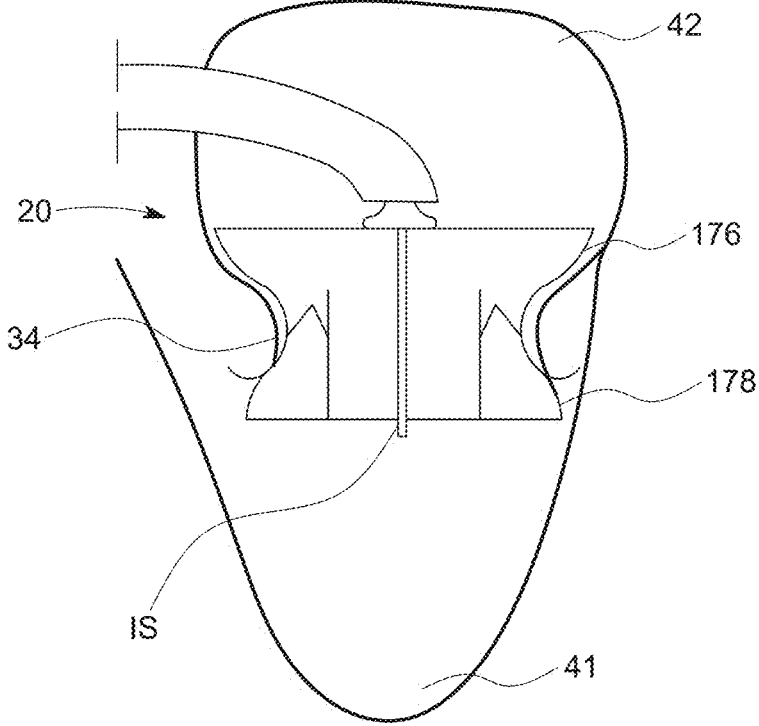

Referring now to FIG. 22C, the valve cover may be further retracted until the atrial anchor 176 is exposed and deploys via self-expansion, as there are no structures preventing such self-expansion once the valve cover clears the atrial anchor 176. As shown in FIG. 22C, at this point the ventricular anchor 178 is still maintained in an exposed but un-deployed condition, with the atrial anchor 176 not in contact (or not in significant contact) with the tissue of the mitral valve annulus 34 on the atrial side. As shown in FIG. 22D, at this point the atrial anchor 176 may be advanced distally into contact with the atrial side of the mitral valve annulus 34, for example by advancing extension catheter 26. At this point, the sutures S may be released from engagement with the ventricular anchor 176. For example, one end of the suture(s) may be pulled proximally from the point of access outside the patient, allowing the other end of the suture to pull through the delivery catheter, release its connection to the ventricular anchor 178 and then be fully removed from the patient. As the suture(s) S disconnect from the ventricular anchor 178, there is nothing remaining to prevent the ventricular anchor 178 from fully deploying into contact with the ventricular side of the mitral valve annulus 34, so that the atrial anchor 176 and ventricular anchor 178 pinch the mitral valve annulus 34 to secure the prosthetic heart valve 20 therein. The internal shaft IS may be withdrawn back into the delivery catheter (or the valve cover may be advanced over the internal shaft IS), and the delivery catheter may be removed from the patient.

Although much of the disclosure above directed specifically to providing two types of steering in the same plane (e.g. medial/lateral steering and "height" steering) is disclosed in the context of wires attached to steering rings, it should be understood that the precise structures that the steering cables attach to are not necessarily critical, and other structures may be suitable. Rather, the positioning of the various "pull" cables relative to each other and relative to the "return" cables (if return cables are included) and relative to any slits or cutouts in the steerable tube are what is more important. In other words, although the word "steering ring" is used frequently herein, unless stated otherwise, a steering "ring" is not limited to a circular enclosed ring, and instead may include a partial ring (e.g. less than 360 degrees) or even other structures such as pins. In other words, although the three-way steering is described in the context of 3 pairs of pull/return cables attached to and/or routed through fully circular steering rings, the relative position of the cables may be identical, but instead those cables may attach to partial rings or even other structures (e.g. pins welded to the steering catheter), and for the purposes of this application, the term "steering ring" encompasses all such structures unless the context requires otherwise.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

The invention claimed is:

1. A method of implanting a medical device into a native atrioventricular heart valve of a patient, the method comprising:

advancing a distal end of a catheter of a delivery system through vasculature of the patient and into an atrium of a heart of the patient;

while the distal end of the catheter is in the atrium, performing a first steering operation to create a first bend at a first location on the catheter and to deflect the distal end of the catheter toward the native atrioventricular heart valve;

after performing the first steering operation, performing a second steering operation to create a second bend at a second location on the catheter and to raise the distal end of the catheter toward a superior wall of the atrium, the second location being positioned proximally to the first location; and after performing the second steering operation, deploying the medical device from the delivery system into or onto the native atrioventricular heart valve of the patient.

2. The method of claim 1, further comprising performing a third steering operation to create a third bend at a third location on the catheter and to move the distal end of the catheter anteriorly or posteriorly, the third steering operation being performed before the second steering operation.

3. The method of claim 2, wherein the third location is positioned proximally of the first location and the second location.

4. The method of claim 1, wherein performing the first steering operation includes tensioning a first steering cable that is coupled to a first steering ring at the first location, and performing the second steering operation includes tensioning a second steering cable that is coupled to a second steering ring at the second location.

5. The method of claim 4, wherein performing the first steering operation includes rotating a first actuator knob on a handle of the delivery system, and performing the second steering operation includes rotating a second actuator knob on the handle of the delivery system, the first actuator knob being different than the second actuator knob.

6. The method of claim 1, wherein the first bend is in a first plane and the second bend is also in the first plane.

7. The method of claim 1, wherein the native atrioventricular heart valve of the patient is a native mitral valve of the patient, and the atrium of the patient is a left atrium.

8. The method of claim 7, further comprising advancing the distal end of the catheter from a right atrium of the patient through an opening in an atrial septum of the patient until the distal end of the catheter is positioned in the left atrium of the patient, and the second steering operation is performed while the catheter extends through the opening in the atrial septum.

9. The method of claim 8, wherein the first steering operation is performed while the catheter extends through the opening in the atrial septum.

10. The method of claim 7, wherein the medical device is a self-expanding prosthetic mitral valve, and deploying the self-expanding prosthetic mitral valve from the delivery system includes allowing the self-expanding prosthetic mitral valve to self-expand into the native mitral valve of the patient.

11. A method of implanting a medical device into a native atrioventricular heart valve of a patient, the method comprising:

advancing a distal end of a catheter of a delivery system through vasculature of the patient and into an atrium of a heart of the patient;

deflecting the distal end of the catheter toward the native atrioventricular heart valve in a first steering operation;

raising a height of the distal end of the catheter toward a superior wall of the atrium in a second steering operation while the distal end of the catheter remains deflected; and after performing the second steering operation, deploying the medical device from the delivery system into or onto the native atrioventricular heart valve of the patient.

12. The method of claim 11, wherein immediately after the first steering operation, the distal end of the catheter is parallel to a longitudinal axis of the native atrioventricular heart valve, and immediately after the second steering operation, the distal end of the catheter is non-parallel to the longitudinal axis of the native atrioventricular heart valve.

13. The method of claim 12, further comprising deflecting the distal end of the catheter back toward the native atrioventricular heart valve in a third steering operation which is performed after the second steering operation but before deploying the medical device.

14. The method of claim 11, wherein the second steering operation tends to move the distal end of the catheter to an orientation that is non-parallel to the longitudinal axis of the native atrioventricular heart valve, and the method includes performing a third steering operation simultaneously while performing the second steering operation, the third steering operation tending to deflect the distal end of the catheter toward the native atrioventricular heart valve so that the distal end of the catheter remains parallel to the longitudinal axis of the native atrioventricular heart valve while the second and third steering operations are simultaneously performed.

15. The method of claim 11, wherein during the second steering operation, the distal end of the catheter remains parallel to a longitudinal axis of the native atrioventricular valve.

16. A method of implanting a medical device into a native atrioventricular heart valve of a patient, the method comprising:

advancing a distal end of a catheter of a delivery system through vasculature of the patient and into an atrium of a heart of the patient;

positioning the distal end of the catheter adjacent to the native atrioventricular heart valve so that the medical device has an orientation that is parallel to a longitudinal axis of the native atrioventricular heart valve;

after the distal end of the catheter is positioned adjacent to the native atrioventricular heart valve, and while the medical device is coupled to the delivery system, raising the distal end of the catheter toward a superior wall of the atrium without changing the orientation of the medical device; and after raising the distal end of the catheter, deploying the medical device from the delivery system into or onto the native atrioventricular heart valve of the patient.

17. The method of claim 16, wherein positioning the distal end of the catheter adjacent to the native atrioventricular heart valve is performed via a first steering operation that deflects the distal end of the catheter toward the native atrioventricular heart valve using a first actuator of the delivery system.

18. The method of claim 17, wherein raising the distal end of the catheter toward the superior wall of the atrium without changing the orientation of the medical device is performed via second and third steering operations performed simultaneously, the second steering operation raising the distal end of the catheter toward the superior wall of the atrium using a second actuator of the delivery system, the third steering operation maintaining the orientation of the medical device using the first actuator of the delivery system.

19. The method of claim 16, wherein raising the distal end of the catheter toward the superior wall of the atrium without changing the orientation of the medical device is performed until a target region of the medical device aligns with the native atrioventricular heart valve.

20. The method of claim 19, wherein prior to raising the distal end of the catheter toward the superior wall of the atrium, the target region is positioned sub-annularly relative to the native atrioventricular heart valve.

* * * * *